(12) United States Patent
Palushi et al.

(10) Patent No.: US 11,583,393 B2
(45) Date of Patent: Feb. 21, 2023

(54) APPARATUS AND METHOD TO MAINTAIN PATENCY OF DILATED ANATOMICAL OPENING

(71) Applicant: Acclarent, Inc., Irvine, CA (US)

(72) Inventors: Jetmir Palushi, Irvine, CA (US); Henry F. Salazar, Pico Rivera, CA (US); Itzhak Fang, Irvine, CA (US); Jeffrey B. Everett, Easton, PA (US)

(73) Assignee: Acclarent, Inc., Irvine, CA (US)

( * ) Notice: Subject to any disclaimer, the term of this patent is extended or adjusted under 35 U.S.C. 154(b) by 41 days.

(21) Appl. No.: 16/681,874

(22) Filed: Nov. 13, 2019

(65) Prior Publication Data

US 2020/0179107 A1 Jun. 11, 2020

Related U.S. Application Data

(60) Provisional application No. 62/775,408, filed on Dec. 5, 2018.

(51) Int. Cl.
*A61F 2/18* (2006.01)
*A61M 29/02* (2006.01)
(Continued)

(52) U.S. Cl.
CPC ............ *A61F 2/186* (2013.01); *A61M 29/02* (2013.01); *A61F 2210/0004* (2013.01);
(Continued)

(58) Field of Classification Search
CPC ............ A61F 2/186; A61F 2210/0004; A61F 2220/0016; A61F 2250/0067; A61F 2/18;
(Continued)

(56) References Cited

U.S. PATENT DOCUMENTS

| 7,720,521 | B2 | 5/2010 | Chang et al. |
| 8,128,680 | B2* | 3/2012 | Arnault De La Menardiere ........ A61F 2/954 623/1.23 |
| 8,444,688 | B2* | 5/2013 | Sherry ................ A61F 2/848 623/1.36 |

(Continued)

FOREIGN PATENT DOCUMENTS

| CN | 107753162 A | 3/2018 |
| EP | 2446915 A1 | 5/2012 |

(Continued)

OTHER PUBLICATIONS

International Search Report and Written Opinion dated Mar. 10, 2020 for International Application No. PCT/IB2019/060244, 19 pages.

*Primary Examiner* — Dinah Baria
(74) *Attorney, Agent, or Firm* — Frost Brown Todd LLP

(57) ABSTRACT

An implant delivery system includes a catheter, an implant, and a push body. The catheter extends from a first proximal end to a first distal end. The catheter defines an inner lumen extending through the first distal end. The implant includes a second proximal, a second distal end, and a plurality of resilient barbs. The implant is slidably housed within the inner lumen. The implant is compressed in the inner lumen such that the implant bears against an inner diameter of the inner lumen and the implant is retained within the inner lumen by friction. The push body is slidably housed within the inner lumen of the catheter. The push body is adjacent to the second proximal end of the implant.

20 Claims, 18 Drawing Sheets

(51) Int. Cl.
*A61M 25/10* (2013.01)
*A61M 25/01* (2006.01)

(52) U.S. Cl.
CPC .......... *A61F 2220/0016* (2013.01); *A61F 2250/0067* (2013.01); *A61M 25/0136* (2013.01); *A61M 25/1018* (2013.01); *A61M 2025/0166* (2013.01); *A61M 2029/025* (2013.01)

(58) Field of Classification Search
CPC ........... A61M 25/10; A61M 25/1018; A61M 25/0136; A61M 25/0102; A61M 29/02; A61M 29/025; A61M 2025/0166
See application file for complete search history.

(56) References Cited

U.S. PATENT DOCUMENTS

| | | | | |
|---|---|---|---|---|
| 9,539,131 | B2* | 1/2017 | Shelso | A61F 2/966 |
| 2009/0209950 | A1* | 8/2009 | Starksen | A61B 5/0535 |
| | | | | 606/21 |
| 2010/0158974 | A1* | 6/2010 | Schomig | A61L 31/08 |
| | | | | 424/423 |
| 2011/0004057 | A1 | 1/2011 | Goldfarb et al. | |
| 2011/0259343 | A1* | 10/2011 | Karabey | A61B 17/12186 |
| | | | | 128/831 |
| 2014/0364725 | A1 | 12/2014 | Makower | |
| 2015/0005805 | A1* | 1/2015 | Kesten | A61F 5/08 |
| | | | | 606/196 |
| 2015/0081017 | A1 | 3/2015 | Abbate et al. | |
| 2016/0008083 | A1 | 1/2016 | Kesten et al. | |
| 2018/0104001 | A1 | 4/2018 | Palushi et al. | |
| 2018/0310886 | A1 | 11/2018 | Salazar et al. | |

FOREIGN PATENT DOCUMENTS

| | | |
|---|---|---|
| EP | 2702964 A1 | 3/2014 |
| EP | 2921138 A1 | 9/2015 |

* cited by examiner

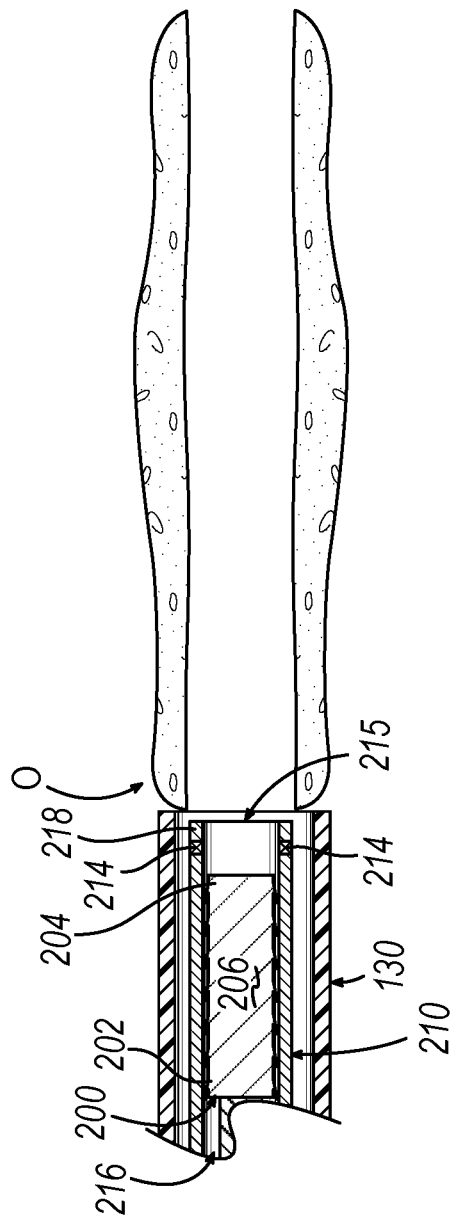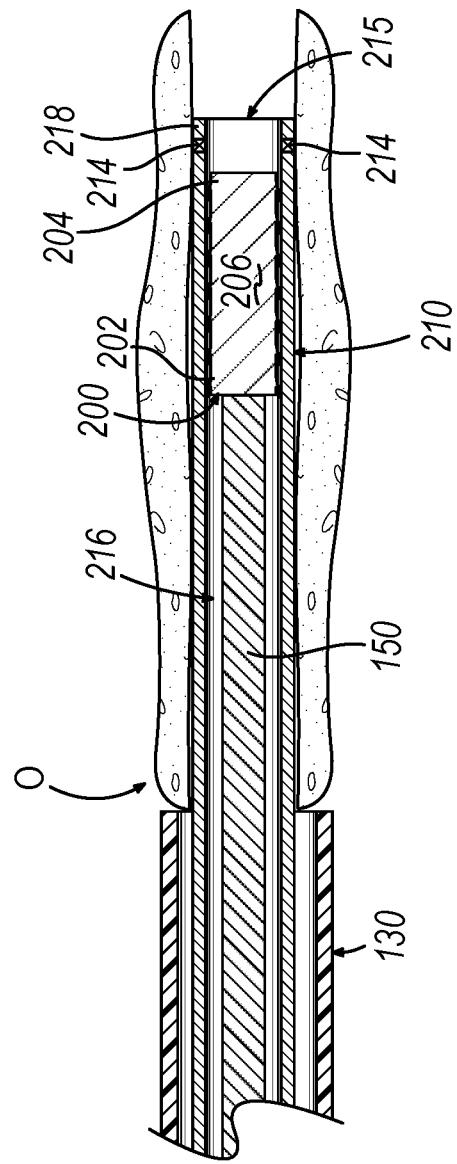
FIG. 8A
FIG. 8B

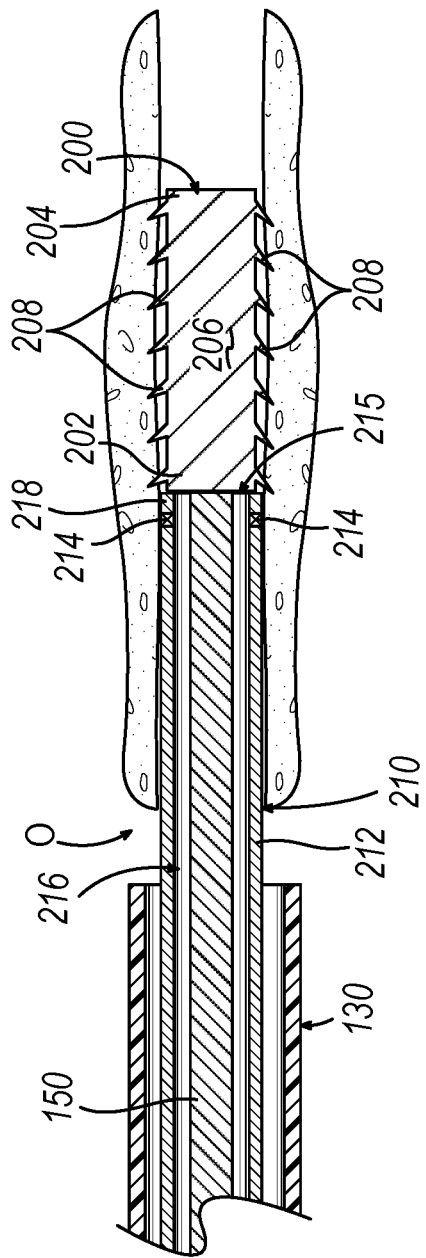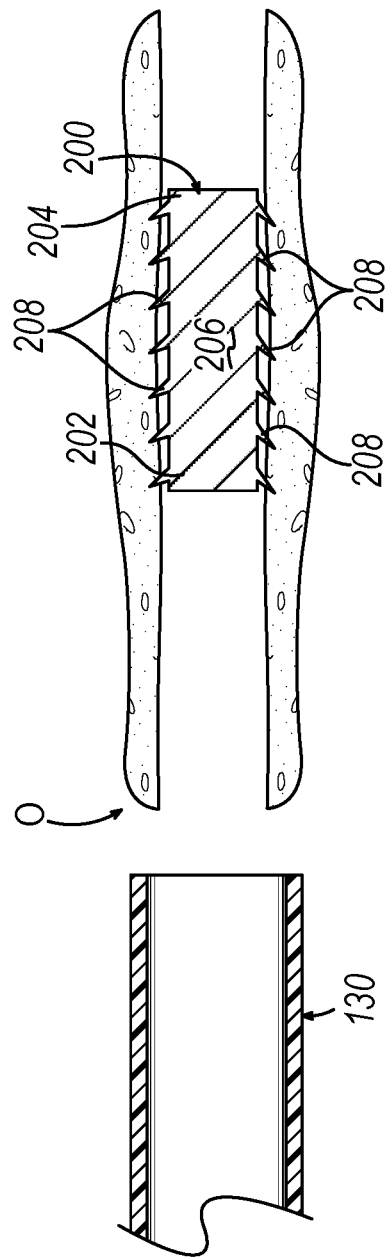
FIG. 8C
FIG. 8D

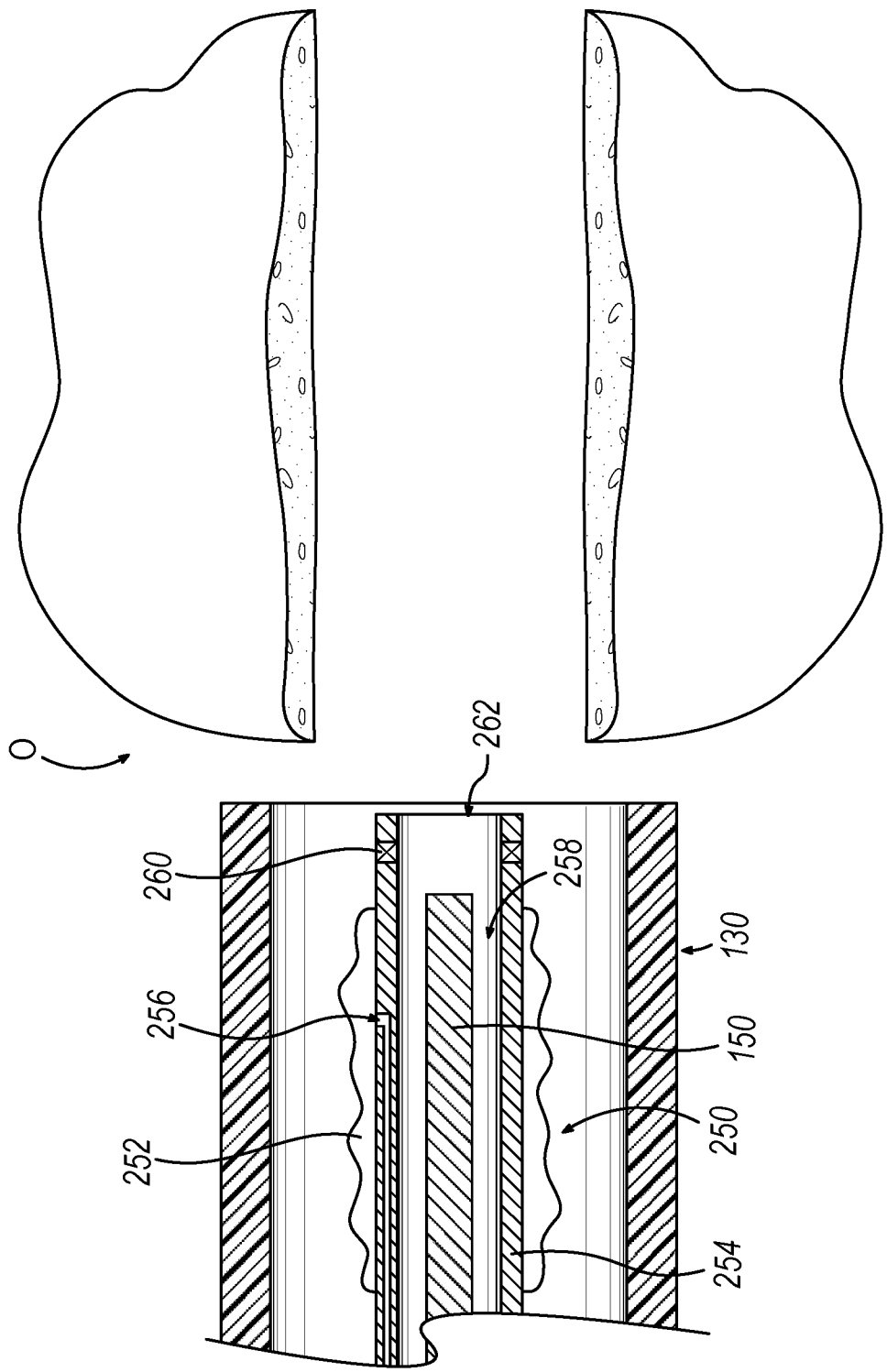

APPARATUS AND METHOD TO MAINTAIN PATENCY OF DILATED ANATOMICAL OPENING

PRIORITY

This application claims priority to U.S. Provisional Pat. App. No. 62/775,408, entitled "Apparatus and Method to Maintain Patency of Dilated Anatomical Opening," filed on Dec. 5, 2018, the disclosure of which is incorporated by reference herein.

BACKGROUND

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, Calif. In some IGS procedures, a digital tomographic scan (e.g., CT or MM, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and guide catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Menlo Park, Calif.

While several systems and methods have been made and used in surgical procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 8A depicts a side cross-sectional view of the guide catheter of the dilation catheter system of FIG. 2 positioned adjacent to an ostium, with the implant delivery catheter of FIG. 6 inserted within the guide catheter near an open distal tip of the guide catheter, where the implant of FIG. 4 is loaded into the lumen of the implant delivery catheter;

FIG. 8B depicts a side cross-sectional view of the guide catheter of the dilation catheter system of FIG. 2 positioned adjacent to the ostium, with the implant delivery catheter of FIG. 6 advanced distally past the open distal tip of the guide catheter within the ostium, where the implant of FIG. 4 is loaded into the lumen of the implant delivery catheter;

FIG. 8C depicts a side cross-sectional view of the guide catheter of the dilation catheter system of FIG. 2 positioned adjacent to the ostium, with the implant delivery catheter of FIG. 6 advanced distally past the open distal tip of the guide catheter within the ostium, where the implant of FIG. 4 is deployed into the ostium;

FIG. 8D depicts a side cross-sectional view of the guide catheter of the dilation catheter system of FIG. 2 positioned adjacent to the ostium, where the implant of FIG. 4 is deployed into the ostium.

FIG. 9A depicts a side cross-sectional view of the guide catheter of the dilation catheter system of FIG. 2 positioned adjacent to the ostium, where an alternative dilation catheter is incorporated in replacement of the dilation catheter of FIG. 2;

Figure 1:
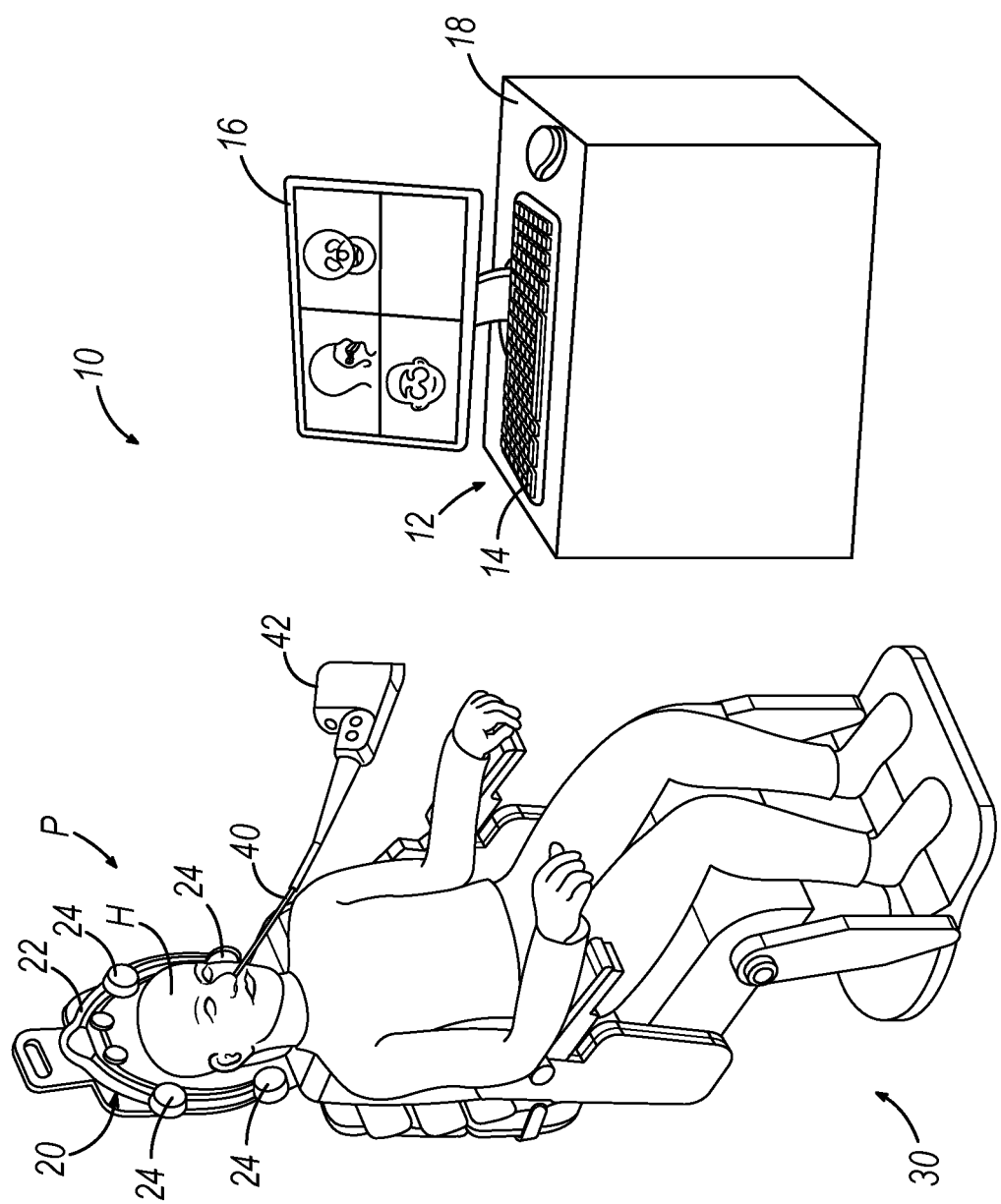
FIG. 1 depicts a schematic view of an exemplary surgery navigation system being used on a patient seated in an exemplary medical procedure chair.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

I. Exemplary Image Guided Surgery Navigation System

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 1 shows an exemplary IGS navigation system (10) enabling an ENT procedure to be performed using image guidance. In addition to or in lieu of having the components and operability described herein IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," (now abandoned) published Dec. 11, 2014, the disclosure of which is incorporated by reference herein.

IGS navigation system (10) of the present example comprises a field generator assembly (20), which comprises set of magnetic field generators (24) that are integrated into a horseshoe-shaped frame (22). Field generators (24) are operable to generate alternating magnetic fields of different frequencies around the head (H) of the patient (P). A navigation guidewire (40) is inserted into the head (H) of the patient (P) in this example. In the present example, frame (22) is mounted to a chair (30), with the patient (P) being seated in the chair (30) such that frame (22) is located adjacent to the head (H) of the patient (P). By way of example only, chair (30) and/or field generator assembly (20) may be configured and operable in accordance with at least some of the teachings of U.S. Patent Pub. No. 2018/0310886, entitled "Apparatus to Secure Field Generating Device to Chair," filed Mar. 23, 2018, issued as U.S. Pat. No. 10,561,370 on Feb. 18, 2020, the disclosure of which is incorporated by reference herein.

Navigation guidewire (40) includes a sensor (not shown) that is responsive to positioning within the alternating magnetic fields generated by field generators (24). Coupling unit (42) may provide wired or wireless communication of data and other signals.

In the present example, the sensor of navigation guidewire (40) comprises at least one coil at the distal end of navigation guidewire (40). When such a coil is positioned within an alternating electromagnetic field generated by field generators (24), the alternating magnetic field may generate electrical current in the coil, and this electrical current may be communicated along the electrical conduit(s) in navigation guidewire (40) and further to processor (12) via coupling unit (42). This phenomenon may enable IGS navigation system (10) to determine the location of the distal end of navigation guidewire (40). A coupling unit (42) is secured to the proximal end of navigation guidewire (40) and is configured to provide communication of data and other signals between console (18) and navigation guidewire (40).

IGS navigation system (10). Such operation includes driving) of the present example further comprises a processor (12), which is operable to drive field generators (24) to generate alternating electromagnetic fields; and process signals from navigation guidewire (40) to determine the location of a sensor in navigation guidewire (40) within the head (H) of the patient (P). Processor (12) of the present example is mounted in a console (18), which comprises operating controls (14) that include a keypad and/or a pointing device such as a mouse or trackball. Processor (12) is further operable to provide video in real time via display screen (16), showing the position of the distal end of navigation guidewire (40) in relation to a video camera image of the patient's head (H), a CT scan image of the patient's head (H), and/or a computer generated three-dimensional model of the anatomy within and adjacent to the patient's nasal cavity. Display screen (16) may display such images simultaneously and/or superimposed on each other during the surgical procedure. By way of example only, display screen (16) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. The images provided through display screen (16) may help guide the operator in maneuvering and otherwise manipulating instruments within the patient's head (H) when such instruments incorporate navigation guidewire (40). It should also be understood that other components of a surgical instrument and other kinds of surgical instruments, as described below, may incorporate a sensor like the sensor of navigation guidewire (40).

II. Overview of Exemplary Dilation Catheter System

Figure 2:
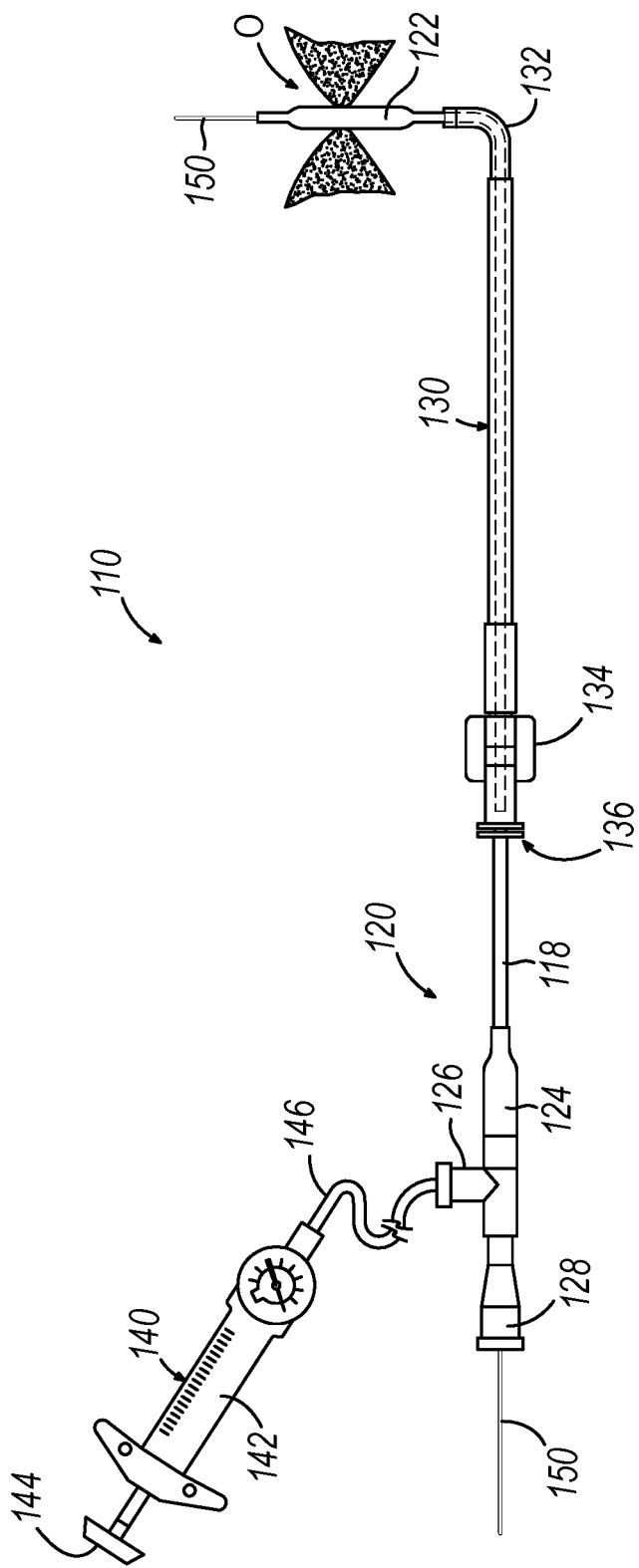
FIG. 2 depicts a side elevational view of an exemplary dilation catheter system.

FIG. 2 shows an exemplary dilation catheter system (110) that may be used to dilate the ostium of a paranasal sinus; or to dilate some other anatomical passageway (e.g., within the ear, nose, or throat, etc.). Dilation catheter system (110) of this example comprises a dilation catheter (120), a guide catheter (130), an inflator (140), and a guidewire (150). By way of example only, dilation catheter system (110) may be configured in accordance with at least some of the teachings of U.S. Patent Pub. No. 2011/0004057, now abandoned, the disclosure of which is incorporated by reference herein.

The distal end of dilation catheter (120) includes an inflatable dilator (122). The proximal end of dilation catheter (120) includes a grip (124), which has a lateral port (126) and an open proximal end (128). A hollow-elongate shaft (118) extends distally from grip (124). Dilation catheter (120) includes a first lumen (not shown) formed within shaft (118) that provides fluid communication between lateral port (126) and the interior of dilator (122). Dilator catheter (120) also includes a second lumen (not shown) formed within shaft (118) that extends from open proximal end (128) to an open distal end that is distal to dilator (122). This second lumen is configured to slidably receive guidewire (150). Dilator (122) may be selectively inflated and deflated by communicating fluid along the first lumen via lateral port (126) while guidewire (150) is positioned within the second lumen.

Guide catheter (130) of the present example includes a bent distal portion (132) at its distal end and a grip (134) at its proximal end. Grip (134) has an open proximal end (136). Guide catheter (130) defines a lumen that is configured to slidably receive dilation catheter (120), such that guide catheter (130) may guide dilator (122) out through bent distal end (132).

Inflator (140) of the present example comprises a barrel (142) that is configured to hold fluid and a plunger (144) that is configured to reciprocate relative to barrel (142) to selectively discharge fluid from (or draw fluid into) barrel (142). Barrel (142) is fluidly coupled with lateral port (126) via a flexible tube (146). Thus, inflator (140) is operable to add fluid to dilator (122) or withdraw fluid from dilator (122) by translating plunger (144) relative to barrel (142).

III. Exemplary Method for Dilating the Ostium of a Maxillary Sinus

Figure 3A:
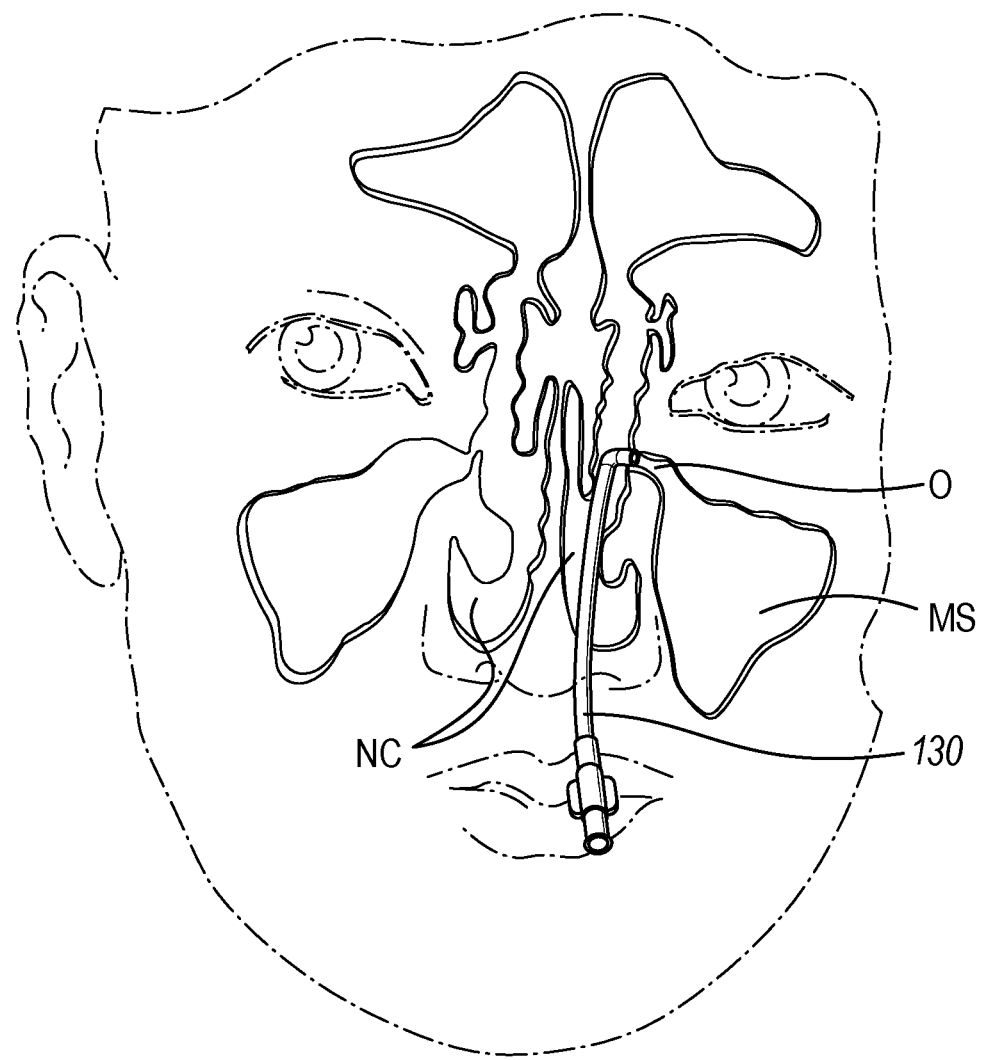
FIG. 3A depicts a front view of a guide catheter of the dilation catheter system of FIG. 2 positioned adjacent an ostium of the maxillary sinus.
Figure 3C:
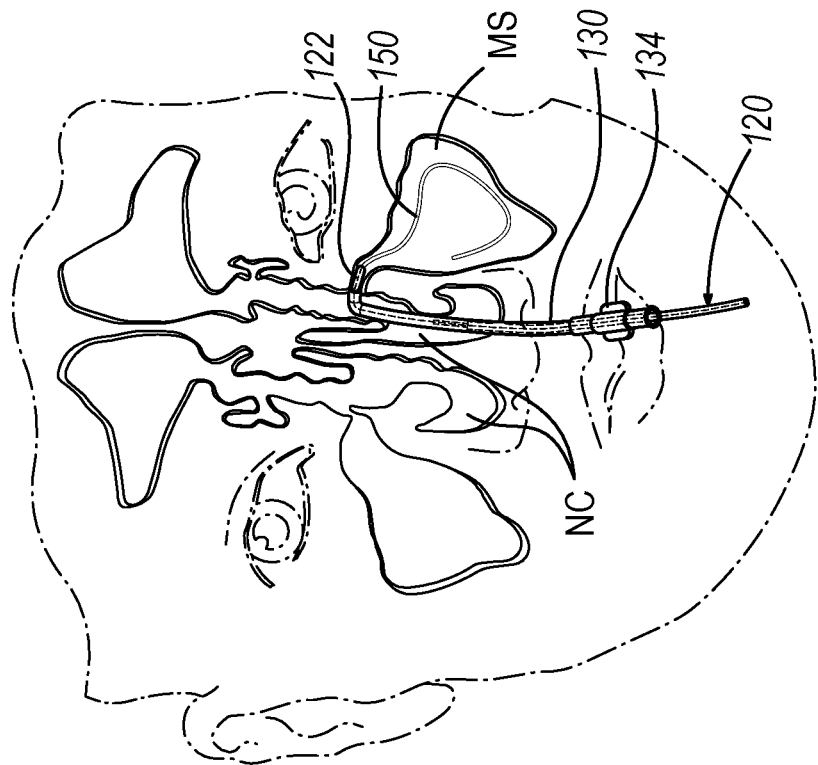
FIG. 3C depicts a front view of the guide catheter of FIG. 3A positioned adjacent an ostium of the maxillary sinus, with the guidewire of FIG. 3B translated further distally relative to the guide catheter and into the maxillary sinus.
Figure 3B:
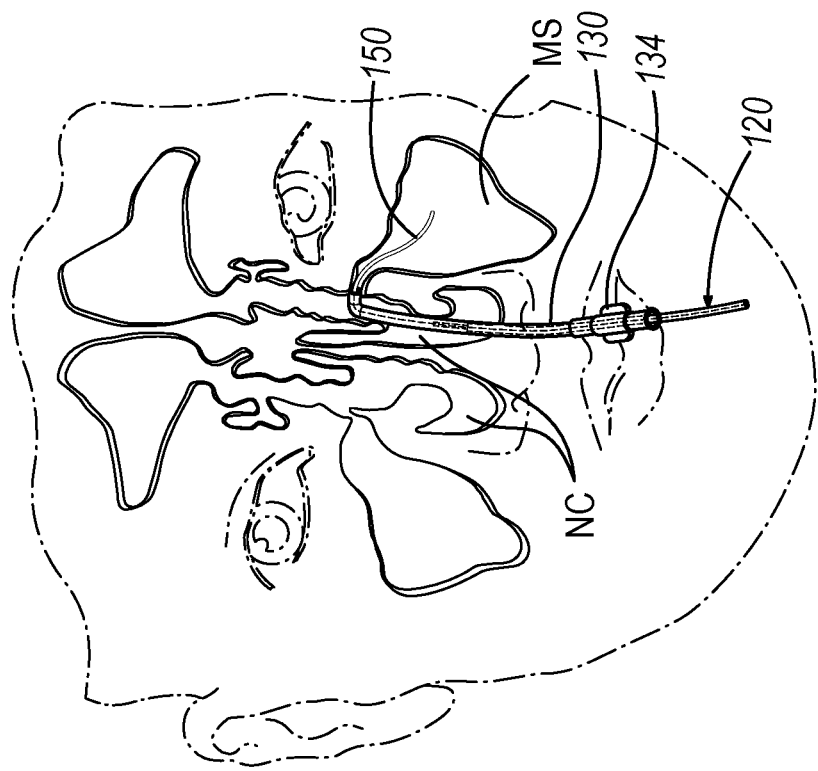
FIG. 3B depicts a front view of the guide catheter of FIG. 3A positioned adjacent an ostium of the maxillary sinus, with a dilation catheter and a guidewire of the dilation catheter system of FIG. 3A positioned in the guide catheter and a distal portion of the guidewire positioned in the maxillary sinus.

FIGS. 3A-3E show an exemplary method for using dilation catheter system (110) discussed above to dilate a sinus ostium (O) of a maxillary sinus (MS) of a patient. In the procedure of the present example, guide catheter (130) may be inserted transnasally and advanced through the nasal cavity (NC) to a position within or near the targeted anatomical passageway to be dilated, the sinus ostium (O), as shown in FIG. 3A. Inflatable dilator (122) and the distal end of guidewire (150) may be positioned within or proximal to bent distal end (132) of guide catheter (130) at this stage. After guide catheter (130) has been positioned, the operator may advance guidewire (150) distally through guide catheter (130) such that a distal portion of the guidewire (150) passes through the ostium (O) of the maxillary sinus (MS) and into the cavity of the maxillary sinus (MS) as shown in FIGS. 3B and 3C. In some instances, guidewire (150) may have illumination capabilities at the distal end of guidewire (150) such that guidewire (150) may provide transcutaneous illumination through the patient's face to enable the operator to visually confirm positioning of the distal end of guidewire (150) in the maxillary sinus (MS) with relative ease.

Figure 3E:
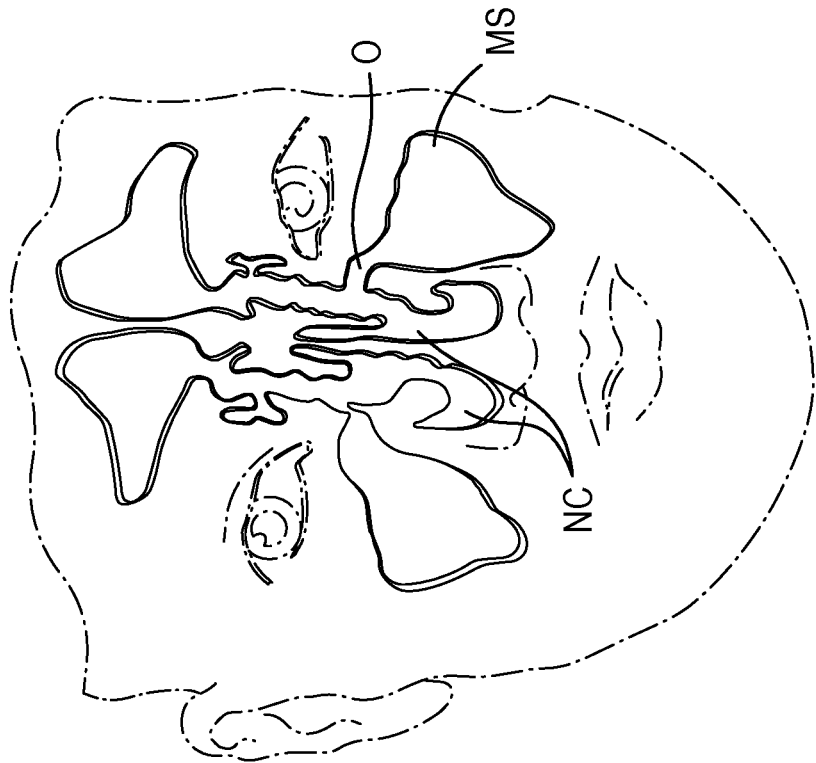
FIG. 3E depicts a front view of an ostium of the maxillary sinus, with the ostium having been enlarged by inflation of the balloon of FIG. 3D.
Figure 3D:
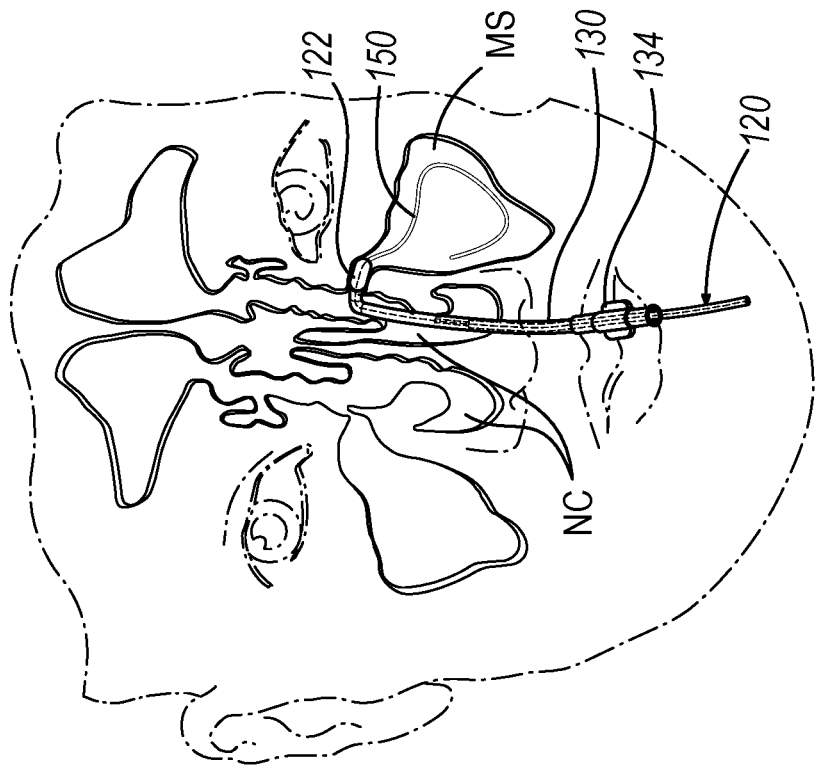
FIG. 3D depicts a front view of the guide catheter of FIG. 3A positioned adjacent an ostium of the maxillary sinus, with the dilation catheter of FIG. 3B translated distally relative to the guide catheter along the guidewire of FIG. 3B so as to position a balloon of the dilation catheter within the ostium.

As shown in FIG. 3C, with guide catheter (130) and guidewire (150) suitably positioned, dilation catheter (120) is advanced along guidewire (150) and through bent distal end (132) of guide catheter (130), with dilator (122) in a non-dilated state until dilator (122) is positioned within the ostium (O) of the maxillary sinus (MS) (or some other targeted anatomical passageway). After dilator (122) has been positioned within the ostium (O), dilator (122) may be inflated, thereby dilating the ostium (O), as shown in FIG. 3D. Inflation of dilator (122) to an expanded state dilates the ostium (O), such as by remodeling the bone, etc., forming ostium (O). Dilator (122) may be repeatedly inflated and deflated in different ostia and/or other targeted anatomical passageways. Thereafter, dilation catheter (120), guidewire (150), and guide catheter (130) may be removed from the patient as shown in FIG. 3E.

IV. Exemplary Implant and Method to Maintain Patency of Dilated Opening

In some instances, a dilated opening such as dilated ostium (O) described above has tissue that may be fluffy, softer than desirable, or otherwise structurally unable to maintain patency through a dilated ostium (O). If tissue surrounding dilated ostium (O) lacks sufficient structural integrity, the tissue may eventually undesirably transition back toward a closed state. In other words, tissue surrounding dilated ostium (O) may undesirably transition such that the opening forming ostium (O) reduces in size. Therefore, it may be desirable to provide a way to prevent closure of a purposefully dilated tubular passageway, such as an ostium (O).

The following description provides various examples of devices and implants that may be deployed within the ostium (O) to provide structural support for the inner diameter of the ostium (O) for a prolonged period of time. Implants described below may irritate the mucosa tissue, eventually generating scar tissue. The scar tissue may be relatively stiff, thereby providing substantially greater structural integrity than the tissue structurally unable to maintain patency through a dilated ostium (O) described above. Therefore, such devices, as well as the scar tissue developed by such devices, may help prevent unwanted reduction in inner diameter of the ostium (O), further closure of the ostium (O), or provide other results. Other suitable ways in which the below-described implants and/or devices may be used will be apparent to those of ordinary skill in the art in view of the teachings herein.

Figure 4:
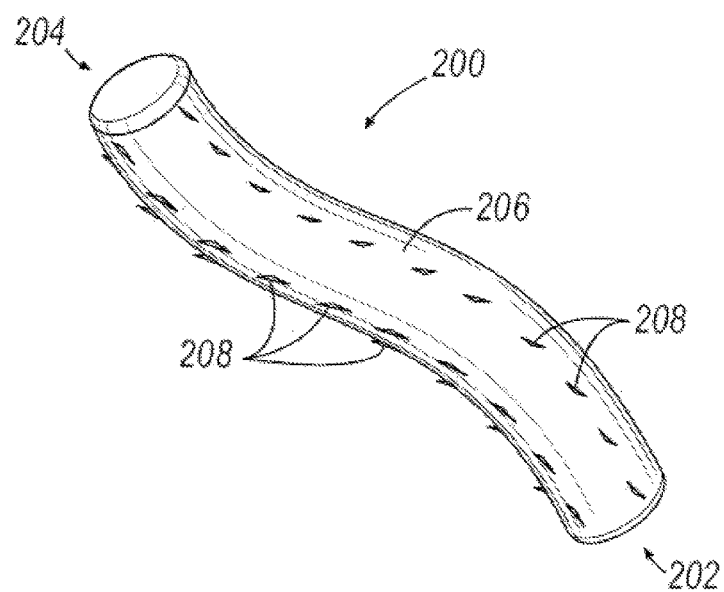
FIG. 4 depicts a perspective view of an exemplary implant that may be inserted into an enlarged ostium, where a plurality of barbs are in a retracted position.
Figures 5A, 5B:
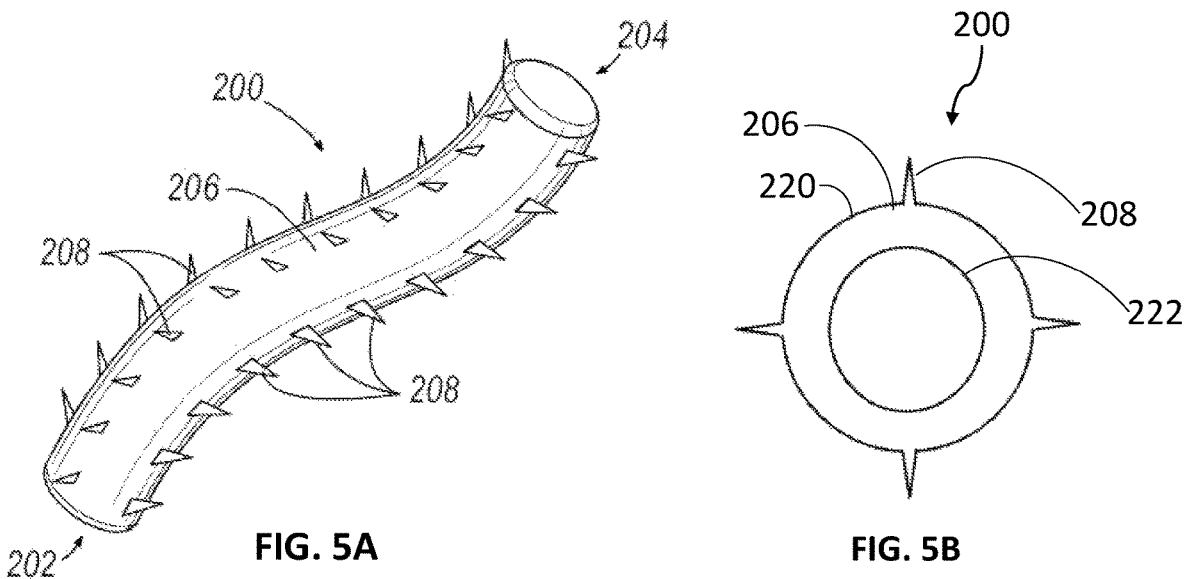
FIG. 5A depicts a perspective view of the implant of FIG. 4, where the plurality of barbs are in an expanded position.
FIG. 5B depicts a cross-sectional view of the implant of FIG. 5A, where the plurality of barbs are in an expanded position.
Figure 6:
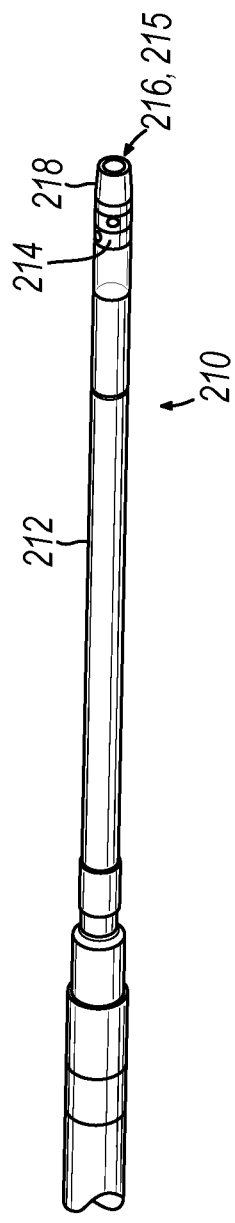
FIG. 6 depicts a perspective view of an implant delivery catheter, where the implant of FIG. 4 is preloaded into a lumen of the implant delivery catheter.
Figure 7:
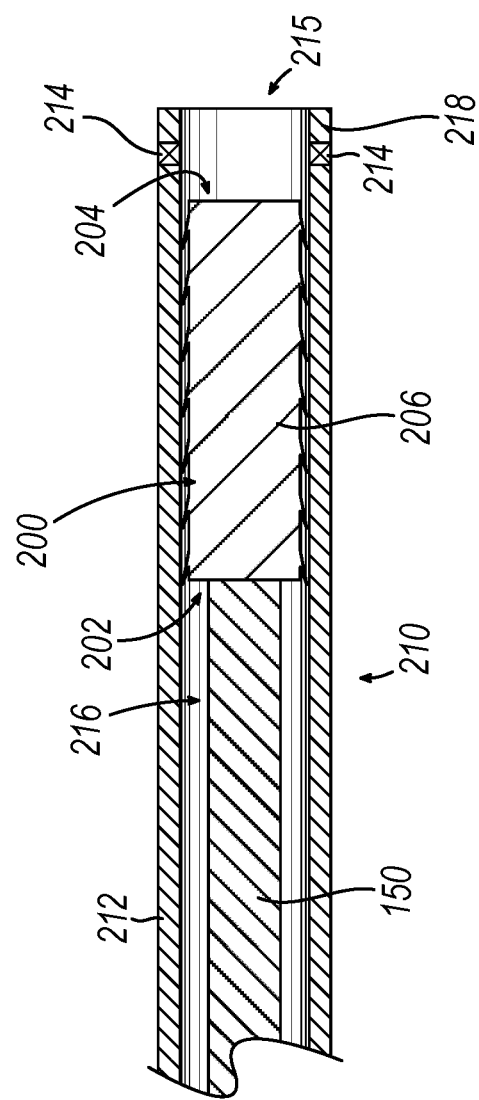
FIG. 7 depicts a side cross-sectional view of implant delivery catheter of FIG. 6, where the implant of FIG. 4 is preloaded into the lumen of the implant delivery catheter.

FIGS. 4-5 show an exemplary implant (200) that may be deployed within an ostium (O), Eustachian Tube, or any other suitable passageway that would be apparent to one having ordinary skill in the art in view of the teachings herein. Therefore, implant (200) may be provided with different lengths, diameters, or other material characteristics based on the targeted passageway. For instance, implant (200) may be suitable for deployment into the frontal recess, which may be longer than an implant for a maxillary sinus ostium. FIG. 6 shows an implant delivery catheter (210) that may be used to house and deploy exemplary implant (200) in accordance with the description herein. As best seen in FIGS. 6-7, implant delivery catheter (210) includes a flexible shaft (212) defining a lumen (216), an open distal tip (218), and a sensor (214) located at open distal tip (218). Lumen (216) extends into distal opening (215) of open distal tip (218). As best shown in FIG. 7, lumen (216) is dimensioned to slidably house implant (200) and guidewire (150). Flexible shaft (212) and lumen (216) may extend proximally into a gripping portion that may define a proximal opening in order to slidably receive guidewire (150) and/or implant (200). Alternatively, implant (200) may be preloaded into a distal end of flexible shaft (212). As will be described in greater detail below, implant delivery catheter (210) and guidewire (150) may be used together in order to suitably deploy implant (200) within a dilated ostium (O).

Sensor (214) may be substantially similar to sensor (not shown) located within navigation guidewire (40) described above. Therefore, sensor (214) may include a coil(s). An electrical conduit(s) may extend proximally from sensor (214) to a coupling unit similar to coupling unit (42) described above. Therefore, when such a coil is positioned within an alternating electromagnetic field generated by field generators (24), the alternating magnetic field may generate position-indicative electrical signals in the coil, and these signals may be communicated along the electrical conduit(s) and further to processor (12) via coupling unit. Therefore, sensor (214) enables use of implant delivery catheter (210) in conjunction with IGS navigation system (10) described above.

Implant (200) includes a body (206) that extends along a longitudinal profile from a proximal portion (202) to a distal portion (204). Body (206) is a longitudinal, cylindraceous body in this example. Body (206) is dimensioned to be inserted into a dilated ostium (O) such that an exterior of body (206) may structurally support tissue/mucosa/submucosa that surrounds ostium (O), which may help prevent ostium (O) from decreasing in size. Body (206) may be dimensioned slightly smaller than the interior surface of a dilated ostium (O). In other examples, body (206) may be dimensioned to engage the interior surface of a dilated ostium (O). Yet in other examples, body (206) may be dimensioned to slightly expand or stretch a dilated ostium (O).

In some instances, body (206) is a longitudinal, cylindraceous body that is configured to be compressible. Therefore, body (206) may be biased toward an expanded or enlarged state by default. Body (206) may be formed of a bioabsorbable, elastomeric material that has elastic properties allowing body (206) to be compressible between the expanded state and a compressed state, as seen between FIGS. 8B-8C. In other words, body (206) may be configured to be radially compressed and axially lengthened when compressed from the original expanded state to the compressed state. For instance, body (206) may be operable to radially compress and axially stretch to a smaller profile upon the application of a predetermined force onto the exterior surface of body (206), thereby transitioning body (206) from the expanded state into the compressed state. As another merely illustrative example, body (206) may radially compress from an expanded state to a compressed state without necessarily also expanding longitudinally. As yet another merely illustrative example, some variations of body (206) are non-compressible.

Body (206) may have any suitable dimension, while in the expanded state, as would be apparent to one skilled in the art in view of the teachings herein. For instance, body (206) may have a diameter ranging between about 5 millimeters to about 9 millimeters. Additionally, body (206) may have a varying radial dimension along the longitudinal profile of body (206). For instance, body (206) may have a longitudinal profile where the proximal portion (202) of body (206) is larger than the distal portion (204) of body (206). As another mere example, body (206) may have a longitudinal profile with an undulating surface. Additionally, the geometrical shape of body (206) may have any suitably shape that would be apparent to one skilled in the art in view of the teachings herein.

The term "implant" should not be read as necessarily requiring the implant (200) to completely block fluid communication through the ostium (O) (though some version of implant (200) may in fact block fluid communication through the ostium (O)). For instance, some versions of implant (200) may operate like a shim. Thus, the term "implant" should be read broadly to include structures like shims. Therefore, body (206) may define one or more longitudinal ventilation channels that enable fluid communication between ends of ostium (O) thereby providing a ventilation pathway. In some instances, implant (200) may have a body (206) similar to a stent. Such a stent may help provide fluid communication through the ostium (O) while sufficiently supporting a recently dilated ostium (O). Any suitable type of stent body may be used as would be apparent to one skilled in the art in view of the teachings herein.

Body (206) may be sufficiently flexible such that portions of body (206) may bend relative to each other to alter the longitudinal profile of body (206). Therefore, body (206) may be sufficiently flexible to conform to the longitudinal profile of ostium (O). The longitudinal profile of body (206), as shown in FIGS. 4-5, is a curve-shape. It should be understood the longitudinal profile of body (206) may flex and change to any suitable profile as would be apparent to one having ordinary skill in the art in view of the teachings herein.

In the current example, a plurality of resilient barbs (208) extend away from the outer surface of body (206). Resilient barbs (208) are biased toward an extended position as shown in FIG. 5. Some resilient barbs (208) are oriented to extend toward proximal portion (202) of body (206), while other resilient barbs (208) are oriented to extend toward distal portion (204) of body (206). This orientation of resilient barbs (208) may provide retention of the implant (200) in each longitudinal direction when implant (200) is suitably deployed. Of course, resilient barbs (208) may extend in any suitable orientation and any suitable pattern of orientations as would be apparent to one having ordinary skill in the art in view of the teachings herein.

Resilient barbs (208) may flex toward body (206) to a retracted position, as shown in FIG. 4, under suitable force. For example, when implant (200) is housed within lumen (216) of implant deliver catheter (210), the interior surface of catheter (210) defining lumen (216) may force resilient barbs (208) into the retracted position. Therefore, once implant (200) is no longer housed within lumen (216) of catheter (210), the resilient nature of resilient barbs (208) may force barbs (208) toward the extended position. Resilient barbs (208) may be configured to suitably engage tissue/mucosa/submucosa surrounding ostium (O) such that when deployed, implant (200) may be substantially fixed relative to ostium (O). Resilient barbs (208) may be configured to puncture tissue. Alternatively, resilient barbs (208) may be configured to sufficiently engage tissue/mucosa/submucosa via sufficient frictional forces.

Body (206) may be made from a bioabsorbable material configured to completely absorb after deployment of implant (200) after any suitable period of time that would be apparent to one skilled in the art in view of the teachings herein. Alternatively, body (206) may be required to be manually removed after deployment of implant (200). Body (206) could be formed of a bundle or braid of barbed sutures. In some versions, body (206) may be formed of an arrangement of concentrically disposed layers (220, 222), where each layer (220, 222) has a different material property. For instance, each layer (220, 222) in the concentrically disposed layers (220, 222) may have a different absorption rate. As another example, each layer (220, 222) may have a different or similar absorption rate, however each layer (220, 222) may include a different therapeutic agent configured to suitably release into ostium (O), as would be apparent to one having ordinary skill in the art in view of the teachings herein. As another example, each layer (220, 222) may provide different functionalities. For example, an outer layer (220) may provide for delivery of a therapeutic agent, while an inner layer (222) may provide for structural integrity. The different types of functionalities will be apparent to one having ordinary skill in the art in view of the teachings herein.

The entirety of implant (200), or selected portions of implant (200), may be coated or otherwise implemented with any suitable drug or therapeutic agent as would be apparent to one skilled in the art in view of the teachings herein. For example, body (206) may be coated with a therapeutic agent. As another mere example, barbs (208) may be coated with a therapeutic agent. In versions incorporating a therapeutic agent, the therapeutic agent may be configured for immediate release. Alternatively, the therapeutic agent may be configured for delayed release. Alternatively still, the therapeutic agent may be configured for sustained delivery over a certain period of time. Some versions may include more than one therapeutic agent, with the different therapeutic agents having different release times or release rates.

FIGS. 8A-8D show an exemplary use of implant delivery catheter (210) in order to deploy implant (200) within a recently dilated ostium (O). Therefore, it should be understood that ostium (O), as shown in FIG. 8A, may have recently been dilated in accordance with the description above, as exemplified in FIGS. 3A-3E. However, instead of removing guide catheter (130) from the position adjacent to ostium (O), as shown between FIGS. 3D-3E, the operator may maintain the adjacent position of guide catheter (130) relative to ostium (O), as shown in FIG. 8A. Alternatively, implant delivery catheter (210) may deploy implant (200) within ostium (O) that has not been recently dilated.

With the distal end of guide catheter (130) positioned adjacent to dilated ostium (O), the operator may advance implant delivery catheter (210) within guide catheter (130) such that open distal tip (218) is proximal relative to the distal end of guide catheter (130). At the moment shown in FIG. 8A, implant (200) is constrained within lumen (216) of flexible shaft (212). Therefore, barbs (208) are in the retracted position due to engagement with the surface defining lumen (216). Implant (200) may be housed within lumen (216) such that distal movement of flexible shaft (212) also moves implant (200). In other words, the frictional forces between implant (200) and flexible shaft (212) may be sufficient such that implant (200) may suitably translate along with flexible shaft (212) during initial placement of implant delivery catheter (210) within guide catheter (130) and ostium (O). However, as will be described in greater detail below, it should be understood that implant (200) may move relative to flexible shaft (212) in response to suitable forces such that implant (200) is slidably housed within lumen (216) of flexible shaft (212).

Next, as shown in FIG. 8B, the operator may distally advance implant delivery catheter (210), implant (200), and guidewire (150), as a unit relative to guide catheter (130), such that implant (200) and open distal tip (218) are within ostium (O). The operator may visualize the placement of implant delivery catheter (210) using IGS navigation system (10) in conjunction with sensor (214) in accordance with the description herein.

A distal end of guidewire (150) may abut against proximal portion (202) of implant (200). In some examples, guidewire (150) may be advanced with implant (200) and delivery catheter (210) into ostium (O), such that guidewire (150) advances with implant (206) from the position shown in FIG. 8A to the position shown in FIG. 8B as a unit. Alternatively, guidewire (150) may be advanced within lumen (216) after implant (200) and implant delivery catheter (210) have been suitably placed within ostium (O) in accordance with the description herein.

When implant (200) is positioned within ostium (O) at the desired location, the operator may utilize implant delivery catheter (210) to deploy implant (200) within ostium (O). In the current example, and shown between FIGS. 8B-8C, the operator may slide flexible shaft (212) proximally while guidewire (150) remains stationary in contact with the proximal portion (202) of implant (200). Guidewire (150) therefore keeps implant (200) longitudinally stationary within ostium (O) while flexible shaft (212) is retracted proximally relative to ostium (O). Alternatively, the operator may actuate guidewire (150) distally while keeping flexible shaft (212) stationary, therefore distally advancing implant (200) out of open distal tip (218) of flexible shaft (212). Guidewire (150) may be sufficiently flexible but with enough column strength so that guidewire (150) does not buckle when helping advance implant (200) relative to flexible shaft (212). Alternatively, guidewire (150) may be stiff and rigid, such that guidewire (150) amounts to a push rod. It should be noted that a push rode does not necessarily have to be stiff and rigid, as a push rod may be longitudinally stiff, but laterally bendable.

Either way, when implant (200) is deployed, as shown in FIG. 8D, barbs (208) and body (206) are no longer constrained in the compressed/restricted position such that barbs (208) and body (206) resiliently return to the natural expanded position. In the current example, with barbs (208) in the natural expanded position, barbs (208) may penetrate tissue of ostium (O) to help initially anchor implant (200) within ostium (O). Therefore body (206) may help maintain a dilated state of ostium (O) such that body (206) may structurally support tissue recently dilated. With implant (200) suitably deployed, the operator may remove guidewire (150) and implant delivery catheter (210) from ostium (O), as shown in FIG. 8D. As mentioned above, in some instances, implant (200) is bioabsorbable such that after a suitable period of time, implant (200) is absorbed by the patient. However, in instances where implant (200) is not bioabsorbable, implant (200) may be removed manually after a suitable period of time. In instances where implant (200) is removed manually, the operator may be required to grasp a suitable portion of implant (200) with a suitable device, and then pull implant (200) with sufficient force to remove implant (200) from ostium. In such instances, resilient barbs (208) may be strong enough to maintain the position of the implant (200) during normal breathing and other patient-associated activity after implant (200) is installed, but resilient barbs (208) will yield when the operatory pulls on implant (200) with sufficient force.

In the example described above, implant delivery catheter (210) is advanced within guide catheter (130) after dilation catheter (120) is advanced along guidewire (150), positioned within the ostium (O), inflated to dilate ostium (O), and then removed from guide catheter (130). However, the use of a separate implant delivery catheter (210) to deliver implant (200) after ostium (O) have been dilated is merely optional. In some instances, implant (200) may be deployed within ostium (O) in conjunction with dilation catheter (120), after dilation catheter (120) had dilated ostium (O) but before dilation catheter (120) has been removed from ostium (O). In such instances, second lumen (not shown) may be dimensioned to slidably receive and constrain implant (200) in a substantially similar fashion as flexible shaft (212) described above.

FIGS. 9A-9I show the use of an alternative dilation catheter (250) that may be used to dilate a targeted ostium (O), as well as deliver implant (200) within recently dilated ostium (O) such that implant may structurally support ostium (O). Dilation catheter (250) may dilate a targeted ostium (O) as well as deliver implant (200) within recently dilated ostium (O) without having to remove dilation catheter (250) from the targeted ostium (O) and/or guide catheter (130).

Alternative dilation catheter (250) includes a dilator (252), a hollow elongate shaft (254) defining a first lumen (256) and a second lumen (258); which may be substantially similar to dilator (122), hollow elongate shaft (118), first lumen (not shown), and second lumen (not shown) described above, respectively, with differences elaborated below. Therefore, first lumen (256) is in fluid communication with dilator (252) such that dilator (252) may transition between an inflated and deflated state in accordance with the description above. Additionally, second lumen (258) may slidably receive guidewire (150) in accordance with the description above. As will be described in greater detail below, second lumen (258) may be substantially similar to lumen (216) described above. Therefore, second lumen (258) may suitably house implant (200) such that implant (200) may move relative to hollow elongate shaft (254) in response to suitable forces such that implant (200) is slidably housed within second lumen (258).

Additionally, alternative dilation catheter (250) includes a sensor (260) located near a distal opening (262) of dilation catheter (250). Sensor (260) may be substantially similar to sensor (not shown) located within navigation guidewire (30) described above. Therefore, sensor (260) may include a coil(s). An electrical conduit(s) may extend proximally from sensor (260) to a coupling unit similar to coupling unit (42) described above. Therefore, when such a coil is positioned within an alternating electromagnetic field generated by field generators (24), the alternating magnetic field may generate electrical current in the coil, and this electrical current may be communicated along the electrical conduit(s) and further to processor (12) via coupling unit. Therefore, sensor (260) enables use of dilation catheter (250) in conjunction with IGS navigation system (10) described above.

Figure 9B:
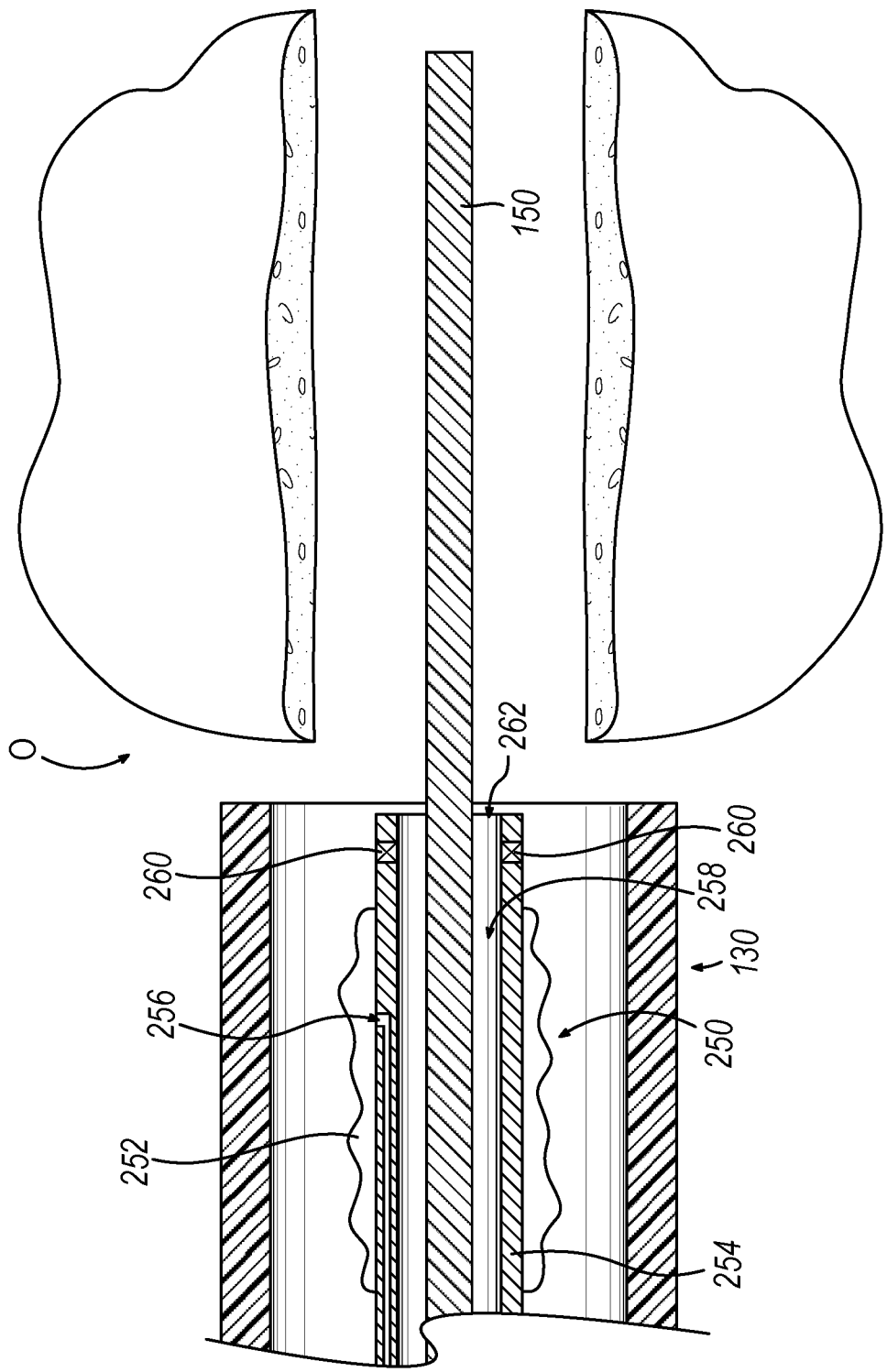
FIG. 9B depicts a side cross-sectional view of the guide catheter of the dilation catheter system of FIG. 2 positioned adjacent to the ostium, where the alternative dilation catheter of FIG. 9A is incorporated in replacement of the dilation catheter of FIG. 2, with the dilation catheter of FIG. 9A and the guidewire of FIG. 3B positioned in the guide catheter and a distal portion of the guidewire positioned in the ostium.

As shown in FIG. 9A, guide catheter (130) may be advanced adjacent to a targeted ostium (O). Dilator (252) and the distal end of guidewire (150) may be positioned within or proximal to bent distal end (132) of guide catheter (130) at this stage. After guide catheter (130) has been positioned, the operator may advance guidewire (150) distally through guide catheter (130) such that a distal portion of the guidewire (150) passes into or through the ostium (O) as shown in FIG. 9B.

Figure 9C:
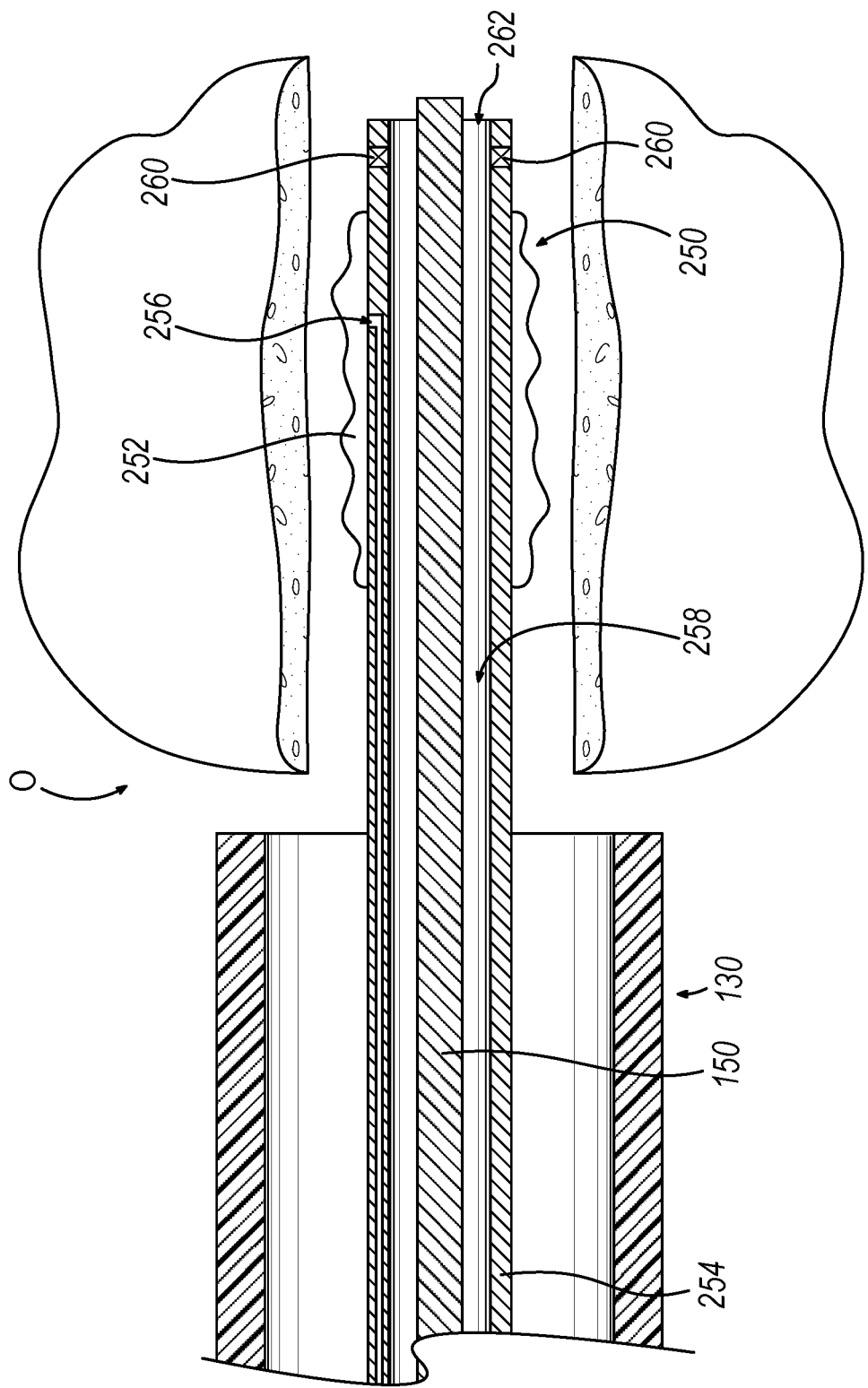
FIG. 9C depicts a side cross-sectional view of the guide catheter of the dilation catheter system of FIG. 2 positioned adjacent to the ostium, where the alternative dilation catheter of FIG. 9A is incorporated in replacement of the dilation catheter of FIG. 2, with the dilation catheter of FIG. 9A translated relative to the guide catheter along the guidewire of FIG. 3B so as to position a balloon of the dilation catheter of FIG. 9A within the ostium.
Figure 9D:
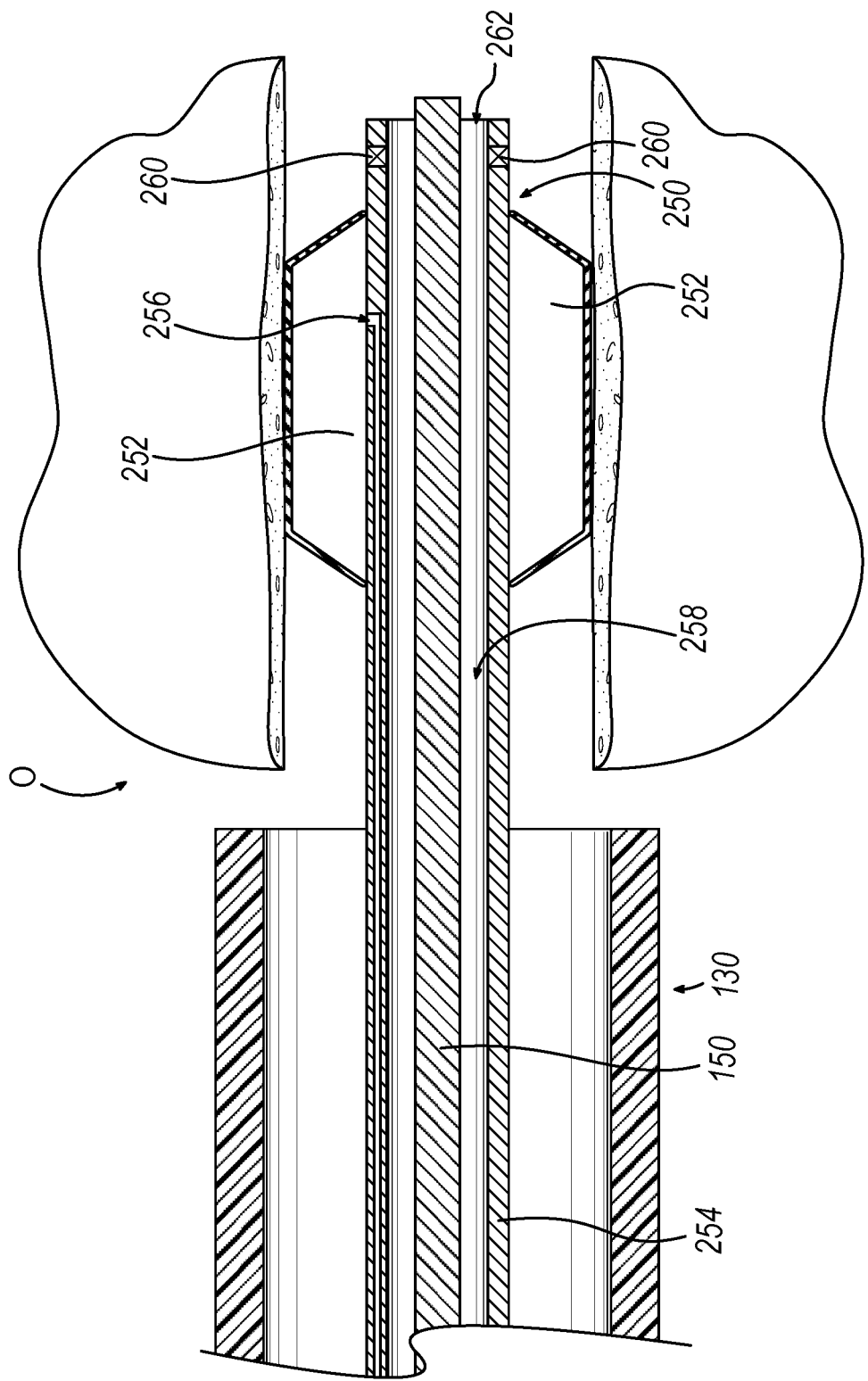
FIG. 9D depicts a side cross-sectional view of the guide catheter of the dilation catheter system of FIG. 2 positioned adjacent to the ostium, where the alternative dilation catheter of FIG. 9A is incorporated in replacement of the dilation catheter of FIG. 2, where the balloon of FIG. 9C is inflated to dilate the ostium.
Figure 9E:
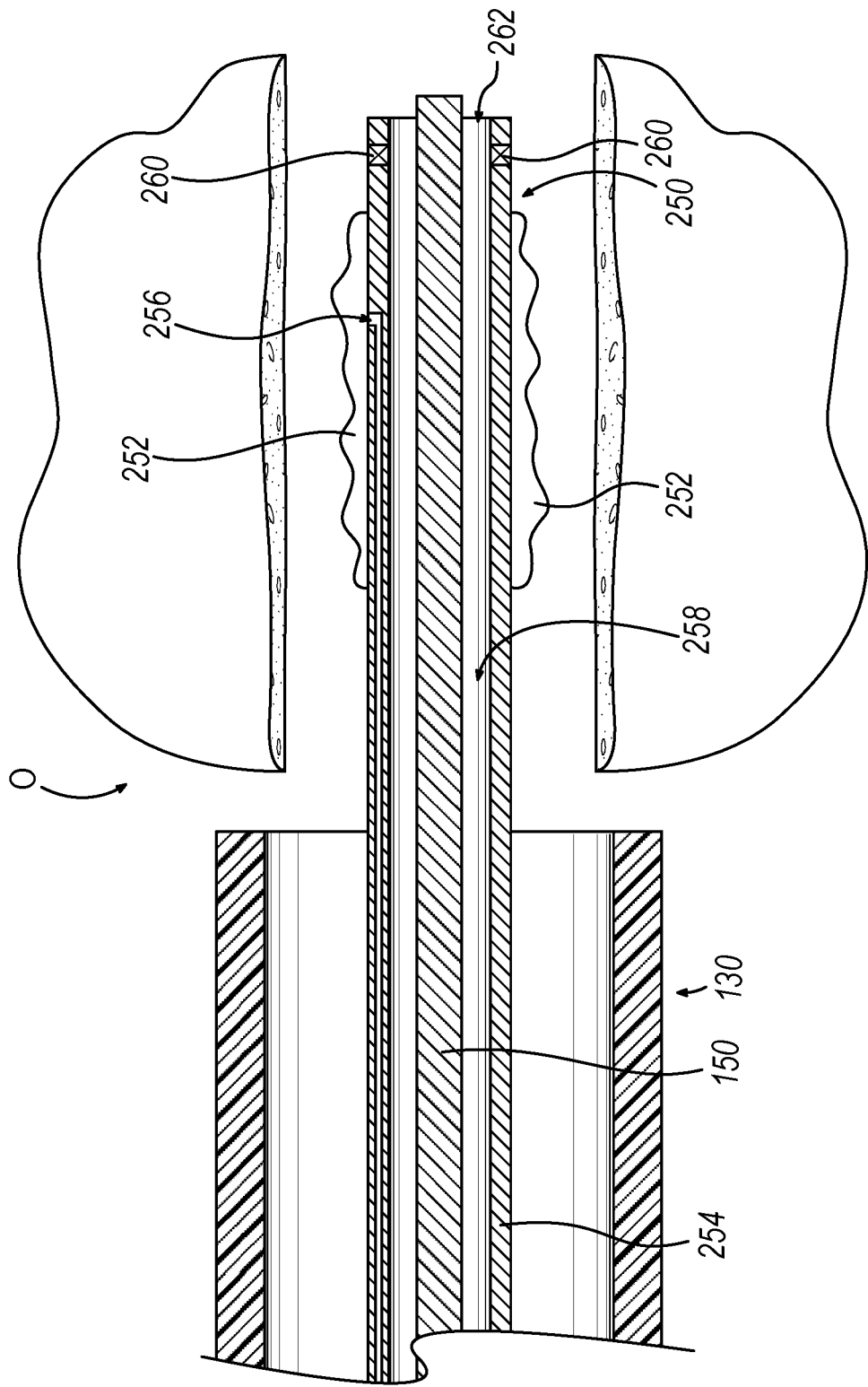
FIG. 9E depicts a side cross-sectional view of the guide catheter of the dilation catheter system of FIG. 2 positioned adjacent to the ostium, where the alternative dilation catheter of FIG. 9A is incorporated in replacement of the dilation catheter of FIG. 2, where the balloon of FIG. 9C is deflated after dilating the ostium.

As shown in FIG. 9C, with guide catheter (130) and guidewire (150) suitably positioned, dilation catheter (250) is advanced along guidewire (150) and through bent distal end (132) of guide catheter (130), with dilator (252) in a non-dilated state until dilator (252) is positioned within the ostium (O) (or some other targeted anatomical passageway). The operator may visualize the placement of dilation catheter (250) using IGS navigation system (10) in conjunction with sensor (260) in accordance with the description herein. After dilator (252) has been positioned within the ostium (O), dilator (252) may be inflated, thereby dilating the ostium (O), as shown in FIG. 9D. After suitably dilating ostium (O) in accordance with the description herein, dilator (252) may then be returned to a non-expanded state as shown in FIG. 9E.

Figure 9F:
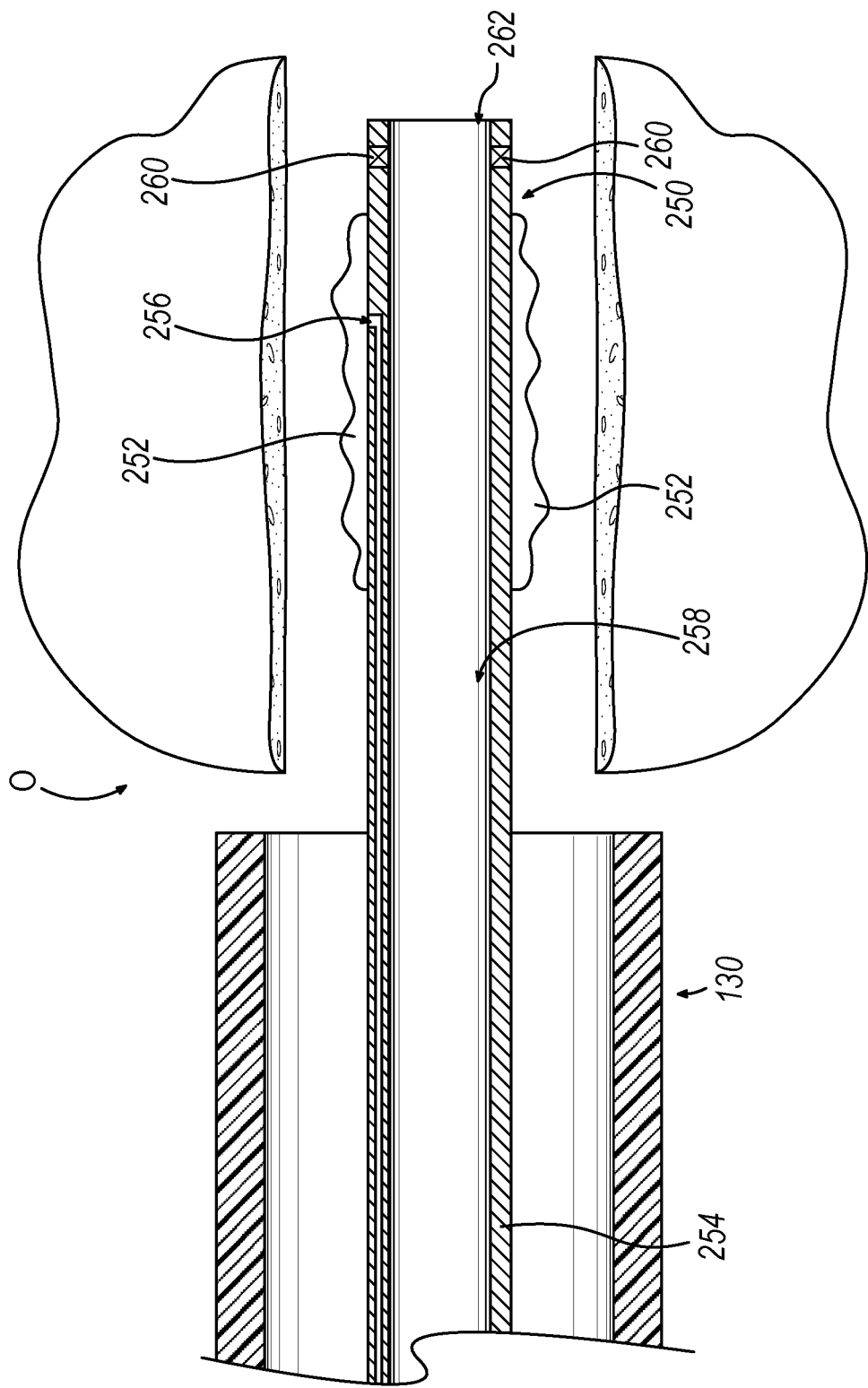
FIG. 9F depicts a side cross-sectional view of the guide catheter of the dilation catheter system of FIG. 2 positioned adjacent to the ostium, where the alternative dilation catheter of FIG. 9A is incorporated in replacement of the dilation catheter of FIG. 2, where the guidewire of FIG. 3B is removed from dilation catheter of FIG. 9A.
Figure 9G:
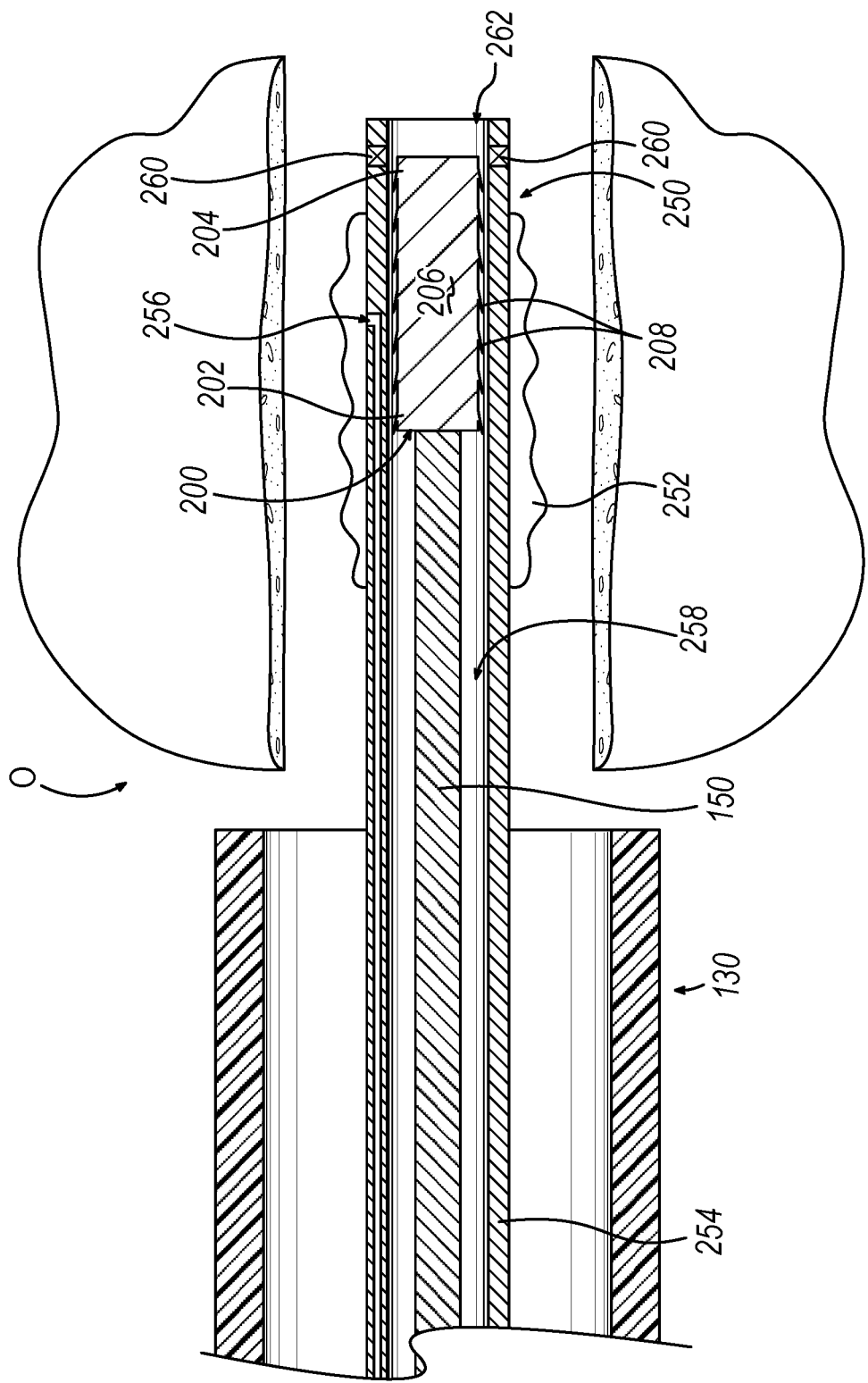
FIG. 9G depicts a side cross-sectional view of the guide catheter of the dilation catheter system of FIG. 2 positioned adjacent to the ostium, where the alternative dilation catheter of FIG. 9A is incorporated in replacement of the dilation catheter of FIG. 2, where the guidewire of FIG. 3B and the implant of FIG. 4A are loaded into the dilation catheter of FIG. 9A within the recently dilated ostium.

Next, guidewire (150) may be removed from the patient as shown in FIG. 9F. Then as shown in FIG. 9G, implant (200) may then be loaded into second lumen (258) and guidewire (150) maybe used to distally actuate implant (200) within second lumen (258) such that implant (200) in housed within second lumen (258) and is directly adjacent to the targeted portion of ostium (O). At the moment shown in FIG. 9G, implant (200) is constrained within second lumen (258) of hollow elongate shaft (254). Therefore, barbs (208) are in the retracted position due to engagement with the surface defining second lumen (258).

When implant (200) is positioned within ostium (O) at the desired location, the operator may utilize guidewire (150) and dilation catheter (250) to deploy implant (200) within ostium (O). In the current example, and shown between FIGS. 9G-9H, the operator may slide hollow elongate shaft (254) proximally while guidewire (150) remains stationary in contact with the proximal portion (202) of implant (200). Guidewire (150) therefore keeps implant (200) longitudinally stationary within ostium (O) while hollow elongate shaft (254) is retracted proximally relative to ostium (O). Alternatively, the operator may actuate guidewire (150) distally while keeping hollow elongate shaft (254) stationary, therefore distally advancing implant (200) out of distal opening (262) of hollow elongate shaft (254). Guidewire (150) may be sufficiently flexible but with enough column strength so that guidewire (150) does not buckle when helping advance implant (200) relative to hollow elongate shaft (254). Alternatively, guidewire (150) may be stiff and rigid, such that guidewire (150) amounts to a push rod.

Figure 9H:
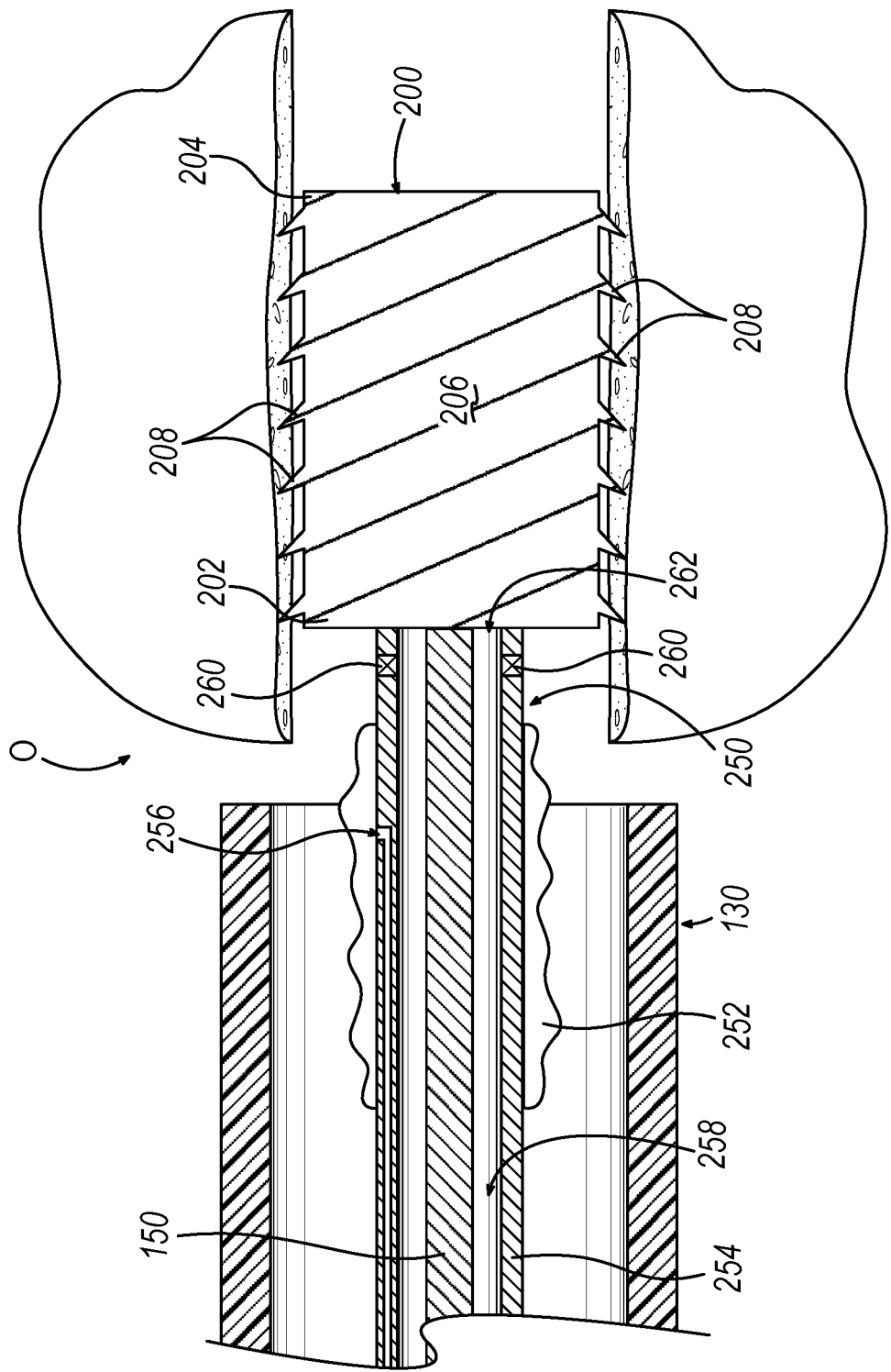
FIG. 9H depicts a side cross-sectional view of the guide catheter of the dilation catheter system of FIG. 2 positioned adjacent to the ostium, where the alternative dilation catheter of FIG. 9A is incorporated in replacement of the dilation catheter of FIG. 2, where dilation catheter of FIG. 9A is moved proximally relative to the guidewire of FIG. 3B and the implant of FIG. 4A, thereby deploying the implant within the recently dilated ostium.
Figure 9I:
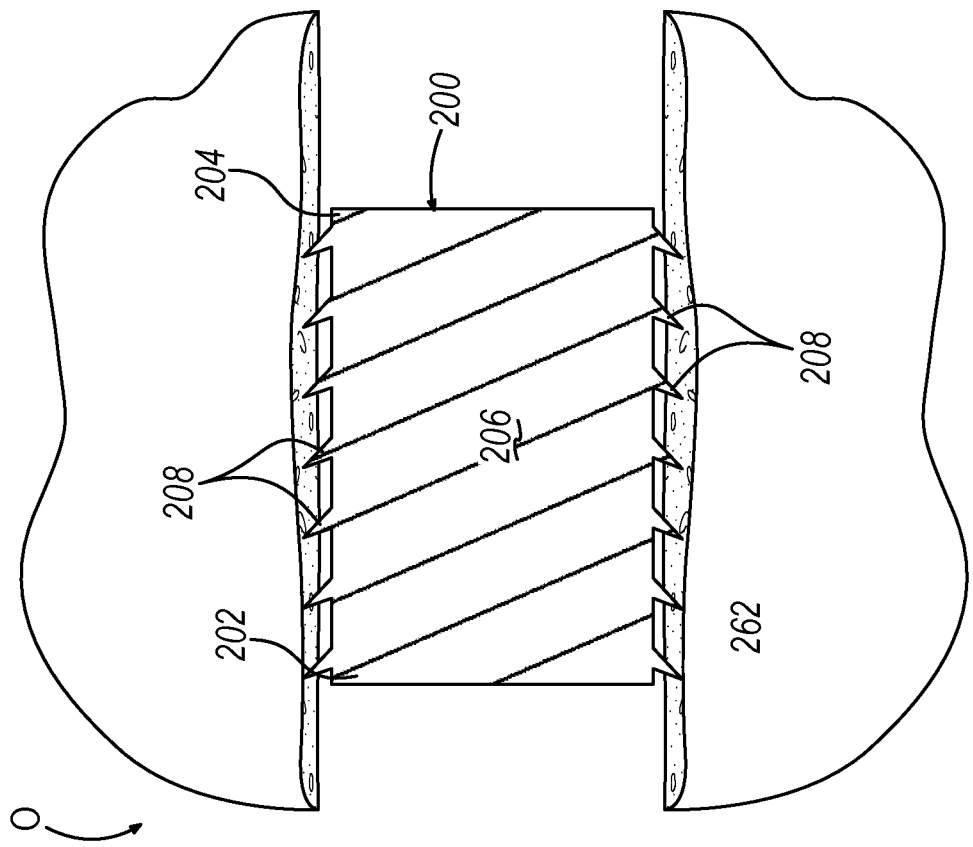
FIG. 9I depicts a side cross-sectional view of the guide catheter of the dilation catheter system of FIG. 2 positioned adjacent to the ostium, where the implant of FIG. 4A is deployed within the recently dilated ostium.
Figure 9I:
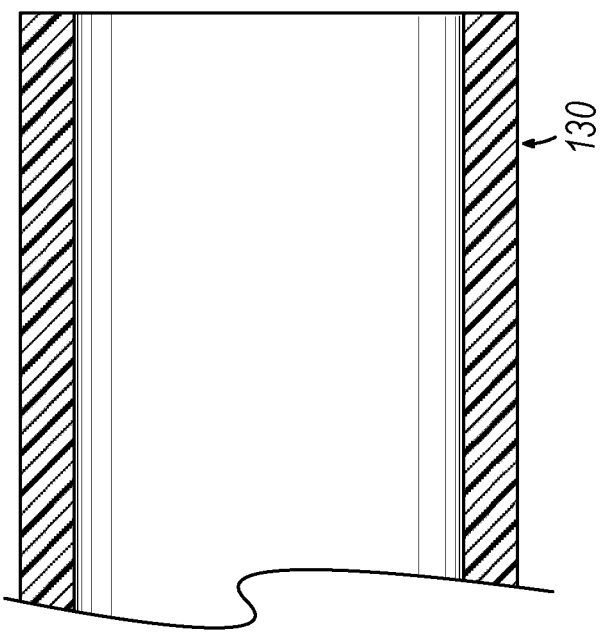

Either way, when implant (200) is deployed, as shown in FIG. 9H, barbs (208) and body (206) are no longer constrained in the compressed/restricted position such that barbs (208) and body (206) resiliently return to the natural expanded position. In the current example, with barbs (208) in the natural expanded position, barbs (208) may penetrate tissue of ostium (O) to help initially anchor implant (200) within ostium (O). Therefore body (206) may help maintain a dilated state of ostium (O) such that body (206) may structurally support tissue recently dilated. With implant (200) suitably deployed, the operator may remove guidewire (150) and dilation catheter (250) from ostium (O), as shown in FIG. 9I. As mentioned above, in some instances, implant (200) is bioabsorbable such that after a suitable period of time, implant (200) is absorbed by the patient. However, in instances where implant (200) is not bioabsorbable, implant (200) may be removed manually after a suitable period of time.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An implant delivery system, comprising: (a) a catheter extending from a first proximal end to a first distal end, wherein the catheter defines an inner lumen extending through the first distal end; (b) an implant, wherein the implant comprises a second proximal, a second distal end, and a plurality of resilient barbs, wherein the implant is slidably housed within the inner lumen, wherein the implant is compressed in the inner lumen such that the implant bears against an inner diameter of the inner lumen and the implant is retained within the inner lumen by friction; and (c) a push body slidably housed within the inner lumen of the catheter, wherein the push body is adjacent to the second proximal end of the implant.

Example 2

The implant delivery system of Example 1, wherein the catheter further comprises a position sensor located adjacent to the first distal end.

Example 3

The implant delivery system of any one or more of Examples 1 through 2, wherein the catheter further comprises a dilator configured to transition between an inflated and deflated state.

Example 4

The implant delivery system of any one or more of Examples 1 through 3, wherein the catheter further defines an inflation lumen in fluid communication with the dilator.

Example 5

The implant delivery system of any one or more of Examples 1 through 4, wherein the catheter comprises a proximal handle.

Example 6

The implant delivery system of any one or more of Examples 1 through 5, wherein the push body comprises a guidewire that is flexible.

Example 7

The implant delivery system of any one or more of Examples 1 through 6, wherein the implant comprises a compressible material configured to transition between a naturally expanded state and a constrained state.

Example 8

The implant delivery system of any one or more of Examples 1 through 7, wherein the implant is at least partially coated with a therapeutic agent.

Example 9

The implant delivery system of any one or more of Examples 1 through 8, wherein the plurality of barbs are resiliently coupled with the implant.

Example 10

The implant delivery system of Example 9, wherein the plurality of barbs are oriented in at least two directions.

Example 11

The implant delivery system of any one or more of Examples 9 through 10, wherein the plurality of barbs configured to yield under sufficient force.

Example 12

The implant delivery system of any one or more of Examples 9 through 11, wherein the plurality of barbs further comprises an annular array of barbs.

Example 13

The implant delivery system of any one or more of Examples 9 through 12, wherein the plurality of barbs further comprises a linear array of barbs.

Example 14

The implant delivery system of and one or more of Examples 1 through 13, wherein the implant is bioabsorbable.

Example 15

A method of using an implant delivery system, where the implant delivery system comprises a catheter defining an inner lumen, an implant, and a push body slidably housed within the inner lumen, wherein the method comprises: (a) positioning a distal end of the catheter within a tubular passageway in a head of a patient; (b) moving the catheter proximally relative to the push body while simultaneously deploying the implant within the tubular passageway by applying a force to a proximal end of the implant; and (c) maintaining the implant in a position within the tubular passageway for a period of time.

Example 16

The method of Example 15, further comprising removing the implant from the tubular passageway.

Example 17

The method of any one or more of Examples 15 through 16, further comprising loading the implant within the inner lumen of the catheter.

Example 18

The method of any one or more of Examples 15 through 17, further comprising moving the implant from a proximal end of the catheter toward the distal end of the catheter by advancing the push bod distally within the inner lumen.

Example 19

A method of using an implant delivery system, where the implant deliver system comprises a dilation catheter defining an inner lumen, an implant, and a guidewire slidably housed within the inner lumen, where the dilation catheter further comprises a dilator, wherein the method comprises: (a) deploying the guidewire through a passageway via a guide catheter, wherein the passageway is in fluid communication with a nasal cavity; (b) advancing the dilator through the guide catheter and over the guidewire to position the dilator within the passageway; (c) expanding the dilator to dilate the passageway; (d) removing the guidewire from the inner lumen of the dilation catheter; (e) loading the implant within the inner lumen of the dilation catheter; (f) advancing the implant distally within the inner lumen to a distal end of the dilation catheter; and (g) moving the dilation catheter proximally relative to the guidewire while simultaneously deploying the implant within the passageway by applying a force to a proximal end of the implant.

Example 20

The method of Example 19, further comprising deflating the dilator with the passageway.

VI. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An implant delivery system, comprising:
   (a) a catheter extending from a first proximal end to a first distal end, wherein the catheter includes an exterior surface and defines an inner lumen extending through the first distal end;
   (b) an implant, wherein the implant comprises a body including a second proximal end, a second distal end, and a plurality of resilient barbs, wherein the implant is slidably housed within the inner lumen, wherein the implant is compressed in the inner lumen such that the implant bears against an inner diameter of the inner lumen and the implant is retained within the inner lumen by friction, wherein the implant is configured to restrict fluid communication through a paranasal sinus passageway or a Eustachian tube, wherein the body further includes a first layer and a second layer, wherein the second layer is concentrically positioned within the first layer, wherein the first layer has a different absorption rate than the second layer;
   (c) a push body slidably housed within the inner lumen of the catheter, wherein the push body is adjacent to and configured to engage the second proximal end of the implant; and
   (d) a dilator configured to transition between an inflated state and a deflated state, wherein the dilator is positioned on the exterior surface of the catheter.

2. The implant delivery system of claim 1, wherein the catheter further comprises a position sensor located adjacent to the first distal end.

3. The implant delivery system of claim 1, wherein the catheter further defines an inflation lumen in fluid communication with the dilator.

4. The implant delivery system of claim 3, wherein, the inflation lumen extends distally between the inner lumen and the exterior surface.

5. The implant delivery system of claim 1, wherein the push body comprises a guidewire that is flexible.

6. The implant delivery system of claim 1, wherein the implant comprises a compressible material configured to transition between a naturally expanded state and a constrained state.

7. The implant delivery system of claim 1, wherein the implant is at least partially coated with a therapeutic agent.

8. The implant delivery system of claim 1, wherein the plurality of resilient barbs is resiliently coupled with the implant.

9. The implant delivery system of claim 8, wherein the plurality of resilient barbs is oriented in at least two directions.

10. The implant delivery system of claim 8, wherein the plurality of resilient barbs is configured to yield under sufficient force.

11. The implant delivery system of claim 8, wherein the plurality of resilient barbs further comprises an annular array of barbs.

12. The implant delivery system of claim 8, wherein the plurality of resilient barbs further comprises a linear array of barbs.

13. The implant delivery system of claim 1, wherein the implant is bioabsorbable.

14. The implant delivery system of claim 1, wherein the implant is configured to block fluid communication through the paranasal sinus passageway or the Eustachian tube.

15. The implant delivery system of claim 1, wherein the push body is configured to be translated distally relative to the catheter and engages the second proximal end of the implant to thereby distally advancing the implant until the second proximal end distally passes the first distal end of the catheter.

16. An implant delivery system comprising:
   (a) a catheter extending from a first proximal end to a first distal end, wherein the catheter defines an inner lumen extending through the first distal end, wherein the catheter is sized and configured to fit within a paranasal sinus passageway or a Eustachian tube;
(b) an implant, wherein the implant comprises a body including a second proximal end, a second distal end, and a plurality of resilient barbs, wherein the implant is slidably housed within the inner lumen, wherein the implant is compressed in the inner lumen such that the implant bears against an inner diameter of the inner lumen and the implant is retained within the inner lumen by friction, wherein the body includes a first layer and a second layer, wherein the second layer is concentrically positioned within the first layer, wherein the first layer has a different absorption rate than the second layer; and
(c) a push body slidably housed within the inner lumen of the catheter, wherein the push body is adjacent to the second proximal end of the implant.

17. The implant delivery system of claim 16, wherein the implant is configured to restrict fluid communication through the paranasal sinus passageway or the Eustachian tube.

18. An implant delivery system, comprising:
(a) a hollow shaft extending from a proximal shaft end to a distal shaft end, wherein the hollow shaft includes an exterior surface and defines an inner lumen extending through the distal shaft end;
(b) an implant, wherein the implant comprises a body including a proximal implant portion including a proximal face, a distal implant portion and a plurality of resilient barbs, wherein the implant is slidably housed within the inner lumen, wherein the implant is compressed in the inner lumen such that the implant bears against an inner diameter of the inner lumen and the implant is retained within the inner lumen by friction, wherein the implant is sized and configured to fit within a paranasal sinus passageway or a Eustachian tube, wherein the body includes a first layer and a second layer, wherein the second layer is concentrically positioned within the first layer, wherein the first layer has a different absorption rate than the second layer;
(c) a push body slidably housed within the inner lumen of the hollow shaft, wherein the push body is adjacent to the implant, wherein the push body is configured to engage the proximal face thereby deploying the implant; and
(d) a dilator configured to transition between an inflated state and a deflated state, wherein the dilator is positioned on the exterior surface of the hollow shaft.

19. The implant delivery system of claim 18, wherein the hollow shaft is configured to translate proximally relative to the implant while the push body remains stationary and engages the proximal face until the distal shaft end of the hollow shaft proximally passes the implant.

20. The implant delivery system of claim 18, wherein, the implant includes an implant axis extending along a length of the implant, wherein the proximal implant portion and the distal implant portion are concentric to the implant axis when slidably housed within the inner lumen, wherein one of the proximal implant portion or the distal implant portion is not concentric to the implant axis when fitted within the paranasal sinus passageway or the Eustachian tube.

* * * * *